US007579321B2

(12) United States Patent
Fein

(10) Patent No.: US 7,579,321 B2
(45) Date of Patent: *Aug. 25, 2009

(54) PHARMACEUTICAL COMPOSITIONS INCLUDING LOW DOSAGES OF DESMOPRESSIN

(75) Inventor: Seymour Fein, New Canaan, CT (US)

(73) Assignee: Reprise Biopharmaceutics, LLC, New City, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/173,074

(22) Filed: Jul. 15, 2008

(65) Prior Publication Data

US 2009/0005432 A1 Jan. 1, 2009

Related U.S. Application Data

(60) Continuation of application No. 11/744,615, filed on May 4, 2007, now Pat. No. 7,405,203, which is a division of application No. 10/706,100, filed on Nov. 12, 2003, which is a continuation-in-part of application No. PCT/US03/14463, filed on May 6, 2003.

(30) Foreign Application Priority Data

May 7, 2002 (GB) ................................. 0210397.6

(51) Int. Cl.
*A61K 38/08* (2006.01)
*C07K 7/04* (2006.01)
(52) U.S. Cl. ........................................ 514/16; 530/326
(58) Field of Classification Search ........................ None
See application file for complete search history.

(56) References Cited

U.S. PATENT DOCUMENTS

| | | | |
|---|---|---|---|
| 3,989,816 A | 11/1976 | Rajadhyaksha | |
| 4,263,283 A | 4/1981 | Cort | |
| 4,285,858 A | 8/1981 | Cort et al. | |
| 4,316,893 A | 2/1982 | Rajadhyaksha | |
| 4,405,616 A | 9/1983 | Rajadhyaksha | |
| 4,557,934 A | 12/1985 | Cooper | |
| 4,588,580 A | 5/1986 | Gale et al. | |
| 4,783,450 A | 11/1988 | Fawzi et al. | |
| 4,863,737 A | 9/1989 | Stanley et al. | |
| 4,878,892 A * | 11/1989 | Sibalis et al. ................. | 604/20 |
| 5,047,398 A | 9/1991 | Hagstam et al. | |
| 5,091,186 A | 2/1992 | Miranda et al. | |
| 5,135,480 A * | 8/1992 | Bannon et al. ................ | 604/20 |
| 5,298,256 A | 3/1994 | Flockhart et al. | |
| 5,441,490 A | 8/1995 | Svedman et al. | |
| 5,482,931 A | 1/1996 | Harris et al. | |
| 5,498,598 A | 3/1996 | Harris et al. | |
| 5,500,413 A | 3/1996 | Larsson et al. | |
| 5,527,288 A | 6/1996 | Gross et al. | |
| 5,534,496 A | 7/1996 | Lee et al. | |
| 5,596,078 A | 1/1997 | Andersson et al. | |
| 5,611,806 A | 3/1997 | Jang et al. | |
| 5,631,246 A | 5/1997 | Hashemi et al. | |
| 5,674,850 A | 10/1997 | Larsson et al. | |
| 5,698,516 A | 12/1997 | Nilsson et al. | |
| 5,707,648 A | 1/1998 | Yiv | |
| 5,726,287 A | 3/1998 | Andersson et al. | |
| 5,763,398 A | 6/1998 | Bengtsson | |
| 5,763,405 A | 6/1998 | Fjellestad-Paulsen et al. | |
| 5,763,407 A | 6/1998 | Larsson et al. | |
| 5,780,434 A | 7/1998 | Fjellestad-Paulsen | |
| 5,840,899 A | 11/1998 | Bedeschi et al. | |
| 5,843,016 A | 12/1998 | Lugnani et al. | |
| 5,843,114 A | 12/1998 | Jang et al. | |
| 5,848,991 A | 12/1998 | Gross et al. | |
| 5,879,326 A | 3/1999 | Godshall et al. | |
| 5,906,831 A | 5/1999 | Larsson et al. | |
| 5,922,680 A | 7/1999 | Fjellestad-Paulsen et al. | |
| 5,932,745 A | 8/1999 | Dushin et al. | |
| 5,948,433 A | 9/1999 | Burton et al. | |
| 5,985,385 A | 11/1999 | Gottfried | |
| 5,985,835 A | 11/1999 | Larsson et al. | |

(Continued)

FOREIGN PATENT DOCUMENTS

EP 0278474 8/1988

(Continued)

OTHER PUBLICATIONS

Doctoral Dissertation, "Absorption and Metabolism of Neurohypophyseal Hormones, with special reference to Desmopressin (dDAVP), in Human Tissue and after Various Routes of Administration", (Fjellestad-Paulsen, Anne M.) May 25, 1996.
Trinh-Trang-Tan et al. "Regulation of UT-A2 Protein in vivo and in vitro", *Journal of the American Society of Nephrology*, (Sep. 2000) vol. 11, No. Program and Abstract Issue, pp. 23A.
Wolfson Philip et al. (1979) "Mechanism of Vasopressin Inhibition of Pancreatic Secretion",*American Journal of Gastroenterology*, vol. 71, No. 5, pp. 490-495.
Jahr S Jonathan et al. (1992) "Effect of Desmopressin Acetate on Hindlimb Perfusion Pressure in Rats: What is the Mechanism?" *Anesthesia & Analgesia*, vol. 75, No. 3, pp. 441-445.
Dixon A.K. et al. (1981) "The Effect of DDAVP on Intravenous Urography", *British Journal of Radiology*, vol. 54, pp. 484-487.

(Continued)

*Primary Examiner*—Andrew D Kosar
(74) *Attorney, Agent, or Firm*—Goodwin Procter LLP

(57) ABSTRACT

The present invention is directed to a pharmaceutical composition comprising 0.5 ng to 20 μg desmopressin and a pharmaceutically acceptable carrier. The present invention is also directed to a pharmaceutical composition comprising desmopressin and a pharmaceutically acceptable carrier, wherein the pharmaceutical composition is effective to establish a steady plasma/serum desmopressin concentration in the range of from about 0.1 picograms desmopressin per mL plasma/serum to about 10.0 picogram desmopressin per mL plasma/serum. Articles of manufacture and methods of using the above invention are also disclosed.

21 Claims, 9 Drawing Sheets

U.S. PATENT DOCUMENTS

| | | | |
|---|---|---|---|
| 5,990,273 A | 11/1999 | Andersson et al. |
| 6,010,478 A | 1/2000 | Bellhouse et al. |
| 6,090,803 A | 7/2000 | Failli et al. |
| 6,139,866 A | 10/2000 | Chono et al. |
| 6,143,722 A | 11/2000 | Melin et al. |
| 6,148,232 A | 11/2000 | Avrahami et al. |
| 6,194,407 B1 | 2/2001 | Failli et al. |
| 6,235,900 B1 | 5/2001 | Failli et al. |
| 6,248,363 B1 | 6/2001 | Patel et al. |
| 6,268,360 B1 | 7/2001 | Failli et al. |
| 6,297,234 B1 | 10/2001 | Failli et al. |
| 6,314,317 B1 | 11/2001 | Willis |
| 6,322,532 B1 | 11/2001 | D'Sa et al. |
| 6,344,451 B1 | 2/2002 | Steffan et al. |
| 6,348,486 B1 | 2/2002 | Argentieri et al. |
| 6,406,455 B1 | 6/2002 | Willis et al. |
| 6,490,483 B2 | 12/2002 | Willis |
| 6,511,974 B1 | 1/2003 | Dusza et al. |
| 6,558,695 B2 | 5/2003 | Luo et al. |
| 6,564,093 B1 | 5/2003 | Ostrow et al. |
| 6,616,627 B2 | 9/2003 | Willis et al. |
| 6,620,807 B1 | 9/2003 | Steffan et al. |
| 6,664,249 B1 | 12/2003 | Ashworth et al. |
| 6,693,082 B2 | 2/2004 | Alonso et al. |
| 6,720,001 B2 | 4/2004 | Chen et al. |
| 6,723,077 B2 | 4/2004 | Pickup et al. |
| 6,746,678 B1 | 6/2004 | Shapiro |
| 6,893,655 B2 | 5/2005 | Flanigan et al. |
| 6,903,091 B2 | 6/2005 | Failli et al. |
| 6,930,932 B2 | 8/2005 | Rentschler |
| 6,939,324 B2 | 9/2005 | Gonnelli et al. |
| 6,945,952 B2 | 9/2005 | Kwon |
| 6,960,184 B2 | 11/2005 | Willis et al. |
| 7,018,653 B2 | 3/2006 | Wannerberger et al. |
| 7,022,340 B2 | 4/2006 | Lomryd et al. |
| 7,022,699 B2 | 4/2006 | Failli et al. |
| 7,027,478 B2 | 4/2006 | Ackley |
| 7,053,083 B2 | 5/2006 | Failli et al. |
| 7,060,708 B2 | 6/2006 | Piccariello et al. |
| 7,074,781 B2 | 7/2006 | Ashworth et al. |
| 7,090,763 B2 | 8/2006 | Gottschling et al. |
| 7,094,545 B2 | 8/2006 | Lomryd et al. |
| 7,097,631 B2 | 8/2006 | Trautman et al. |
| 7,097,776 B2 | 8/2006 | Govinda Raju et al. |
| 7,138,393 B2 | 11/2006 | Molinari et al. |
| 7,150,409 B2 | 12/2006 | Gonnelli et al. |
| 7,153,845 B2 | 12/2006 | Levine et al. |
| 7,180,274 B2 | 2/2007 | Chen et al. |
| 7,182,747 B2 | 2/2007 | Kwon |
| 7,187,969 B2 | 3/2007 | Willis |
| 7,383,084 B2 | 6/2008 | Stern et al. |
| 7,405,203 B2 * | 7/2008 | Fein ............ 514/16 |
| 2002/0013262 A1 | 1/2002 | Alonso et al. |
| 2002/0016562 A1 | 2/2002 | Cormier et al. |
| 2002/0082543 A1 | 6/2002 | Park et al. |
| 2002/0107265 A1 | 8/2002 | Chen et al. |
| 2002/0128599 A1 | 9/2002 | Cormier et al. |
| 2002/0178196 A1 | 11/2002 | Monier |
| 2002/0198191 A1 | 12/2002 | Failli et al. |
| 2003/0018024 A1 | 1/2003 | Failli et al. |
| 2003/0054044 A1 | 3/2003 | Potter et al. |
| 2003/0087892 A1 | 5/2003 | Ashworth et al. |
| 2003/0119728 A1 | 6/2003 | Scheidl et al. |
| 2003/0134845 A1 | 7/2003 | Molinari et al. |
| 2004/0018241 A1 | 1/2004 | Houze et al. |
| 2004/0038962 A1 | 2/2004 | Ashworth et al. |
| 2004/0063628 A1 | 4/2004 | Piccariello et al. |
| 2004/0115167 A1 | 6/2004 | Cormier et al. |
| 2004/0138098 A1 | 7/2004 | Fein |
| 2004/0138610 A1 | 7/2004 | Cormier et al. |
| 2004/0220080 A1 | 11/2004 | Lomryd et al. |
| 2004/0242686 A1 | 12/2004 | Isawa et al. |
| 2004/0249339 A1 | 12/2004 | Willis et al. |
| 2004/0265365 A1 | 12/2004 | Daddona et al. |
| 2005/0004103 A1 | 1/2005 | Koshio et al. |
| 2005/0019392 A1 | 1/2005 | Lomryd et al. |
| 2005/0075328 A1 | 4/2005 | Failli et al. |
| 2005/0089554 A1 | 4/2005 | Cormier et al. |
| 2005/0096586 A1 | 5/2005 | Trautman et al. |
| 2005/0106226 A1 | 5/2005 | Cormier et al. |
| 2005/0153873 A1 | 7/2005 | Chan et al. |
| 2005/0154350 A1 | 7/2005 | Willis et al. |
| 2005/0158378 A1 | 7/2005 | Wannerberger et al. |
| 2005/0232997 A1 | 10/2005 | Nilsson et al. |
| 2006/0025387 A1 | 2/2006 | Hochman |
| 2006/0040970 A1 | 2/2006 | Izumimoto et al. |
| 2006/0093658 A1 | 5/2006 | Sathyan et al. |
| 2006/0122113 A1 | 6/2006 | Pinchasi et al. |
| 2006/0122170 A1 | 6/2006 | Koshio et al. |
| 2006/0154916 A1 | 7/2006 | Ashworth et al. |
| 2006/0161111 A1 | 7/2006 | Potter et al. |
| 2006/0183734 A1 | 8/2006 | Failli et al. |
| 2006/0189939 A1 | 8/2006 | Gonnelli et al. |
| 2006/0193825 A1 | 8/2006 | Musso et al. |
| 2006/0200069 A1 | 9/2006 | Cormier et al. |
| 2006/0233871 A1 | 10/2006 | Stern et al. |
| 2006/0240068 A1 | 10/2006 | Lomryd et al. |
| 2006/0241172 A1 | 10/2006 | Zhou et al. |
| 2006/0241176 A1 | 10/2006 | Stack et al. |
| 2006/0247276 A1 | 11/2006 | Gross et al. |
| 2006/0252696 A1 | 11/2006 | Lomryd et al. |
| 2006/0253061 A1 | 11/2006 | Anderson et al. |
| 2006/0258712 A1 | 11/2006 | Jacobson |
| 2006/0258714 A1 | 11/2006 | Heffernan et al. |
| 2006/0258739 A1 | 11/2006 | Ai et al. |
| 2007/0027427 A1 | 2/2007 | Trautman et al. |
| 2007/0032410 A1 | 2/2007 | Quay et al. |
| 2007/0265207 A1 | 11/2007 | Fein |
| 2008/0274951 A1 | 11/2008 | Fein |
| 2009/0042970 A1 | 2/2009 | Herschkowitz et al. |

FOREIGN PATENT DOCUMENTS

| | | |
|---|---|---|
| WO | WO-02/064193 | 8/2002 |
| WO | WO-02/074286 | 9/2002 |
| WO | WO-03/094885 | 11/2003 |
| WO | WO-03/094886 A2 | 11/2003 |
| WO | WO-03/094886 A3 | 11/2003 |
| WO | WO-2004/041153 A3 | 5/2004 |
| WO | WO-2004041153 | 5/2004 |
| WO | WO-2005041871 | 5/2005 |
| WO | WO-2005046707 | 5/2005 |
| WO | WO-2006/060106 | 6/2006 |
| WO | WO-2006/138719 | 12/2006 |
| WO | WO-2007/002523 | 1/2007 |
| WO | WO-2007/083323 | 7/2007 |
| WO | WO-2007/127976 | 11/2007 |
| WO | WO-2009021007 | 2/2009 |

OTHER PUBLICATIONS

Malan T. Philip et al. (1994) "Subcutaneous Administration of Desmopressin as a Test of Maximal Urinary Concentrating Ability in the Fischer 344 Rat", *Toxicology Methods*, vol. 4, No. 3, pp. 188-192.

Tormey William Patrick & O'Laoire Sean Arthur (1992) "Severe Prolonged Antidiuresis Following Desmopressin and Carbamazepine Interaction in Postoperative Diabetes Insipidus", *European Journal of Internal Medicine*, vol. 3, pp. 341-343.

Patent Cooperation Treaty (PCT) International Search Report; International Application No. PCT/US03/14463, mailed on May 27, 2004.

Patent Cooperation Treaty (PCT) International Search Report; International Application No. PCT/US03/35662, mailed on Sep. 30, 2004.

Vilhardt H et al. (1986) "Plasma Kinetics of DDAVP in Man", *Acta Pharmacol Toxicol (Copenh)*, 58 (5): 379-381.

"FDA Notice: Information for Healthcare Professionals Desmopressin Acetate (marketed as DDAVP Nasal Spray, DDAVP Rhinal Tube, DDAVP, DDVP, Minirin, and Stimate Nasal Spray)" available at http://www.fda.gov/cder/drug/InfoSheets/HCP/desmopressinHCP.htm (last visited Jan. 3, 2008).

"Minirin Nasal Spray". Ferring Pharmaceuticals. Internet document <<http://www.medsafe.gov.nz/Consumers/CMI/m/MinirinNSpray.htm>&g-t;, May 3, 2001; accessed Oct. 4, 2007; 3 pages. cited by examiner.

Cormier et al. (2004) "Transdermal delivery of desmopressin using a coated microneedle array patch system," *Journal of Controlled Release* 97:503-511.

Gill et al. (2007) "Coated microneedles for transdermal delivery," *J. Control Release* 117(2):227-237.

Kwon (2004) "In vitro evaluation of transdermal drug delivery by a micro-needle patch," *Controlled Release Society 31$^{st}$ Annual Meeting Transactions*, #115.

Kwon. (2007) "Dissolvable microneedle patch for biopharmaceuticals delivery and vaccination," *Drug Delivery Report* Winter 2007/2008:56-57.

Meyer et al. (1988) "Successful transdermal administration of therapeutic doses of a polypeptide to normal human volunteers," *Clin. Pharmacol. & Therapeutics* 44(6):607-612.

Meyer et al. (1990) "Transdermal versus subcutaneous leuprolide: a comparison of acute pharmacodynamic effect," *Clin. Pharmacol. & Therapeutics* 48(4):340-5.

Pai-Thakur et al. (2007) "Technology Update: Minimally Invasive Injections: Dream or Reality?" *American Association of Indian Pharmaceutical Scientists* 17(4): 9-10.

Park et al. (2006) "Polymer microneedles for controlled-release drug delivery," *Pharm. Res.* 23(5):1008-1019.

Svedman et al. (1991) "Administration of antidiuretic peptide (DDAVP) by way of suction de-epithelialized skin," *The Lancet* 337:1506-1509.

Wermeling et al. (2008) "Microneedles permit transdermal delivery of a skin-impermeant medication to humans," *PNAS* 105(6):2058-2063.

Agnoli et al. (2002) "Low-dose desmopressin infusion: renal action in healthy women in moderate salt retention and depletion, and interactions with prostanoids," Prostaglandins Leukotrienes and Essential Fatty Acids 67(4): 263-273.

Grossman et al. (1980) "Two New Modes of Desmopressin (DDAVP) Administration," British Medical Journal 280(6225): 1215.

Janknegt et al. (1997) "Oral Desmopressin as a New Treatment Modality for Primary Nocturnal Enuresis in Adolescents and Adults: A Double-Blind, Randomized, Multicenter Study," Journal of Urology 157(2): 513-517.

Supplementary European Search Report (2008) for European Application No. EP03781836 (4 pages).

Robinson (1976) "DDAVP in the Treatment of Central Diabetes Insipidus," N Engl J Med 294: 507-511.

Swain (1999) "Blister Packaging Leads the Way: Despite continous pressure to contain costs, the demand for pharmaceutical packages keeps growing," Pharma and Medical Packaging News Magazine (4 pages).

Kohler et al. (1988) "Pharmacokinetics and haematological effects of desmopressin," Eur J Clin Pharmacol 35: 281-285.

Fjellestad-Paulsen et al., "Pharmacokinetics of 1-deamino-8-D-arginine vasopressin after various routes of administration in healthy volunteers," Clinical Endocrinology (1993) 38, pp. 177-182.

Kauli et al. (1985) "Treatment of Diabetes insipidus in Children and Adolescents," *Front. Horm. Res.* 13:304-313.

\* cited by examiner

PHARMACEUTICAL COMPOSITIONS INCLUDING LOW DOSAGES OF DESMOPRESSIN

CROSS-REFERENCE TO RELATED APPLICATIONS

This application is a continuation application of U.S. patent application Ser. No. 11/744,615, filed May 4, 2007, which is a divisional application of U.S. patent application Ser. No. 10/706,100, filed Nov. 12, 2003, which is a Continuation-In-Part Application of PCT Application PCT/US03/14463, filed May 6, 2003, each of which is herein incorporated by reference in its entirety.

BACKGROUND OF THE INVENTION

1. Field of the Invention

This invention relates to pharmaceutical compositions including desmopressin, and more particularly to pharmaceutical compositions including low dosages of desmopressin for treatment of certain human diseases.

2. Brief Description of the Related Art

Desmopressin (1-desamino-8-D-arginine vasopressin, dDAVP) is an analogue of vasopressin. Desmopressin has decreased vasopressor activity and increased antidiuretic activity compared to vasopressin. This pharmacological profile enables desmopressin to be clinically used for antidiuresis without causing significant increases in blood pressure. Desmopressin is commercially available as the acetate salt both in tablet form and as a nasal spray, and is commonly prescribed for voiding postponement, incontinence, primary nocturnal enuresis (PNE) and nocturia, among other indications, including central diabetes insipidus.

Desmopressin has been administered intravenously, subcutaneously, intranasally and orally. The intravenous route of administration is clinically used almost exclusively to treat patients with mild hemophilia or Von Willebrand's Disease to raise blood levels of Factor VIII prior to surgery. Subcutaneous injection is used infrequently and primarily in patients with central diabetes insipidus, a deficiency of vasopressin resulting in the renal production of large volumes of extremely dilute urine which can cause severe dehydration. Intranasal administration of desmopressin via a nasal spray is approved for the maintenance treatment of patients with central diabetes insipidus and in children (ages 6 to 16 years) with primary nocturnal enuresis. An oral tablet dosage form of desmopressin is also approved for the treatment of central diabetes insipidus and primary nocturnal enuresis.

Currently, approved labeling for desmopressin recommends dosing in the following ranges depending on the clinical indication and the route of administration:

| Clinical Indication | Route of Administration (% Bioavailability) | Dose Range (daily) |
|---|---|---|
| Hemophilia/Von Willebrand's | Intravenous (100) | 0.3 mcg/kg (21 mcg for 70 kg patients) |
| Central Diabetes Insipidus (CDI) | Intravenous (100) | 2-4 mcg qd or 1-2 mcg bid |
| | Subcutaneous (±90) | 2-4 mcg qd or 1-2 mcg bid |
| | Intranasal (3-5) | 5-40 mcg qd or 5-20 mcg bid |
| | Oral (0.1) | 100-600 mcg bid |
| Primary Nocturnal Enuresis (PNE) | Intranasal (3-5) | 10-40 mcg qhs |
| | Oral (0.1) | 200-600 mcg qhs |

The maximum plasma/plasma/serum concentrations achieved with a typical intranasal dose of desmopressin for CDI or PNE of 20 micrograms (mcg or μg) would be approximately 20-30 pg/mL based on 3-5% bioavailability. For the desmopressin oral tablet with only 0.1-0.15% bioavailability, a standard dose of 200-400 mcg would also produce a peak plasma/plasma/serum level of 20-30 pg/mL.

While existing formulations of desmopressin have met the needs of patients, there is still a need for improvement. Tablets are often preferred by patients because of their ease of use, discretion and the lack of uncertainty of correct administration. However, tablets generally need to be taken with a glass of water or other drink, which is a problem as fluid intake needs to be restricted in connection with desmopressin treatment, and the message to the patient is much clearer when there is no water intake at all. In addition, while the above doses and plasma/plasma/serum concentrations are effective for treating CDI and PNE, standard dosages of desmopressin have been shown to cause undesirable side-effects including high incidences of hyponatremia. Lower dosages are preferable if the same desired effect could be produced. However, the current trend in this field is the evaluation of higher dosages of desmopressin for treatment purposes.

SUMMARY OF THE INVENTION

In one aspect, the present invention is directed to a pharmaceutical composition, comprising 0.5 ng to 20 μg desmopressin and a pharmaceutically acceptable carrier.

In another aspect, the present invention is directed to a pharmaceutical composition, comprising desmopressin and a pharmaceutically acceptable carrier, wherein the pharmaceutical composition is effective to establish a steady plasma/plasma/serum desmopressin concentration in the range of from about 0.1 picograms desmopressin per mL plasma/plasma/serum to about 10.00 picogram desmopressin per mL plasma/plasma/serum.

In another aspect, the present invention is directed to an article of manufacture comprising packaging material and a pharmaceutical composition contained within the packaging material, wherein the pharmaceutical composition is therapeutically effective for treating or preventing hemophilia, Von Willebrand's Disease, incontinence, primary nocturnal enuresis (PNE), nocturia, or central diabetes insipidus, and wherein the packaging material comprises a label which indicates that the pharmaceutical composition can be used for treating or preventing hemophilia, Von Willebrand's Disease, incontinence, primary nocturnal enuresis (PNE), nocturia, or central diabetes insipidus, and wherein the pharmaceutical composition comprises 0.5 ng to 20 μg desmopressin and a pharmaceutically acceptable carrier In another aspect, the present invention is directed to a method of treating or preventing a disease or condition which is treatable or preventable by desmopressin, the method comprising administering to a patient a daily dose of a therapeutically effective amount of a pharmaceutical composition comprising 0.5 ng to 20 μg desmopressin and a pharmaceutically acceptable carrier.

In another aspect, the present invention is directed to methods of inducing antidiuretic effects in a patient, comprising the step of administering to a patient a daily dose of a therapeutically effective amount of a pharmaceutical composition comprising 0.5 ng to 20 μg desmopressin and a pharmaceutically acceptable carrier.

These and other aspects will become apparent upon reading the following detailed description of the invention.

BRIEF DESCRIPTION OF THE FIGURES

The invention will be more fully understood from the following detailed description taken in conjunction with the accompanying figures in which.

DETAILED DESCRIPTION OF THE INVENTION

Figure 1:
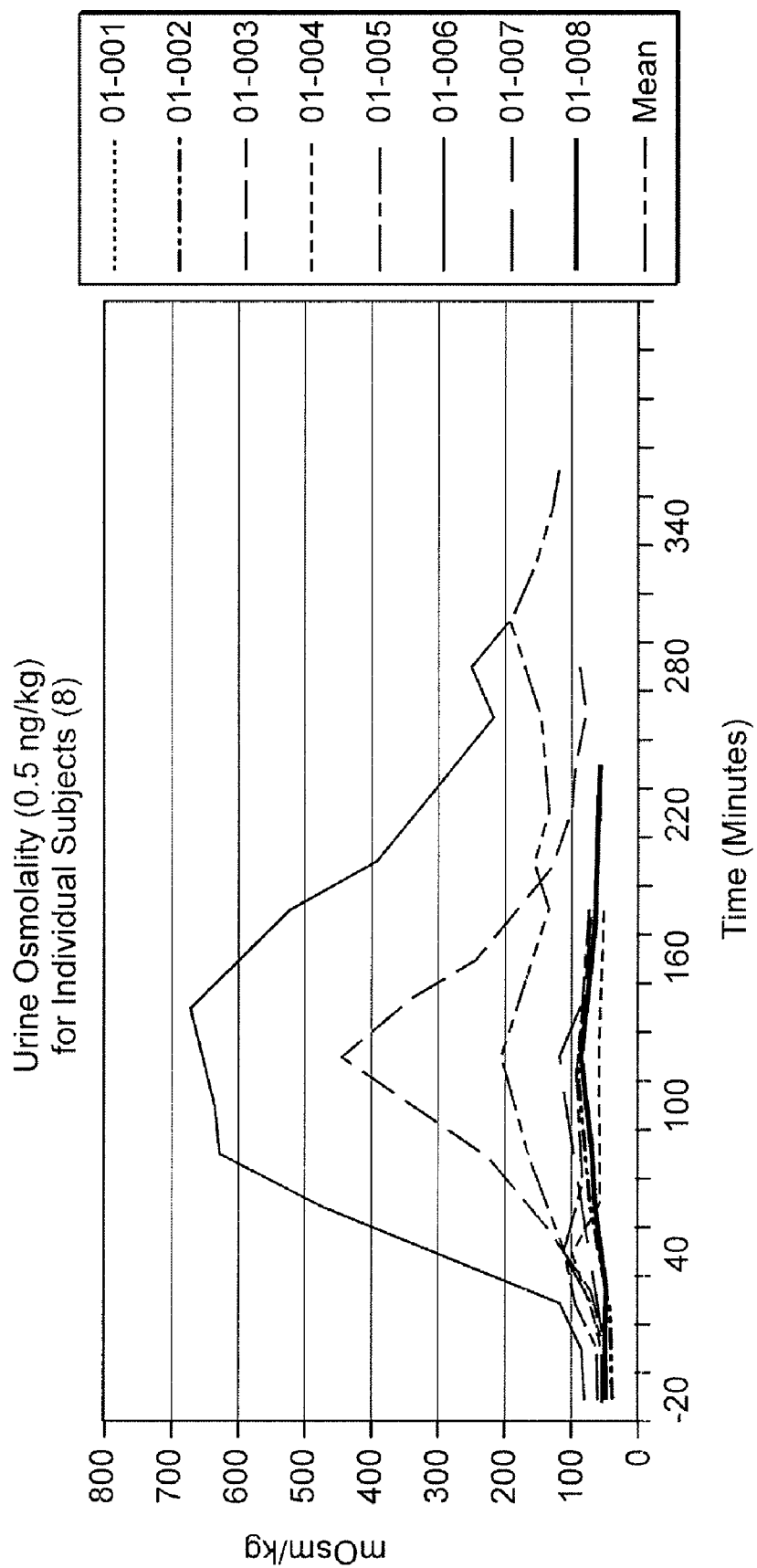
FIG. 1 shows urine osmolality for each subject as a result of administration of 0.5 ng/kg of desmopressin.

It has now been discovered that desmopressin can be administered as a solid dosage form which is absorbed from the mouth and which provides improved bioavailability. It is surprising that desmopressin can be absorbed at all in this way, since the available evidence showed that desmopressin administered in the oral cavity (sub-lingually) was not significantly absorbed (Fjellestad-Paulsen A. et al., *Clin. Endocrinol* 38 177-82 (1993)). It is even more unexpected that bioavailability can be improved compared to a conventional per oral tablet formulation (i.e. which is swallowed by the patient).

It has also been unexpectedly discovered that low doses and plasma/plasma/serum levels of desmopressin are pharmacologically active and can achieve desired therapeutic efficacy. The present inventor has found that doses and plasma/plasma/serum concentrations of desmopressin which are from 5 to 40% of the current recommended doses and resulting plasma/plasma/serum levels are therapeutically effective, and in some cases safer for treatment of CDI, PNE, and additional clinical indications requiring pharmacological concentration of the urine. It has been discovered that the actual dose response curve of desmopressin is shifted to the left relative to current theory and practice and that at each plasma/plasma/serum concentration point over the dose range predicted an incremental pharmacological effect in terms of urine concentration is observed.

According to a first aspect of the invention, there is provided a pharmaceutical dosage form of desmopressin adapted for sublingual absorption.

The desmopressin may be in the form of the free base or a pharmaceutically or, where appropriate veterinarily, acceptable salt, or in any other pharmaceutically or veterinarily acceptable form. The acetate salt is particularly preferred.

The formulation will typically be solid. It may disperse rapidly in the mouth. Such formulations are termed 'orodispersible'. The formulation will typically comprise a suitable carrier for this purpose, which will be pharmaceutically acceptable (or veterinarily acceptable in the case of administration to non-human animals).

The daily dosage of desmopressin, measured as the free base, will generally be from 0.5 or 1 μg to 1 mg per dosage form. In one preferred dosage range, the dosage will typically range from 2 μg to 800 μg per dosage form and preferably from 10 μg to 600 μg. Comparatively lower doses (e.g., lower dosages relative to the dosages above or provided in the art) are also specifically contemplated, for example from 0.5 ng to 20,000 ng, preferably 0.05 mcg (50 ng) to 10 mcg (10,000 ng), and more preferably 0.1mcg (100 ng) to 2000 ng. When one dosage form per day is administered, as is usual for PNE and nocturia, this will typically be the dose per dosage form. When the daily dose is administered in two or more dosages, as will typically be the case for central diabetes insipidus, the amount of the active compound per dosage form will be reduced accordingly. The effective daily dosage will depend on the condition of the individual patient, and is thus within the ordinary skill of the art to determine for any particular patient. Other active ingredients, whether or not peptides, may also be present.

Pharmaceutical dosage forms of the present invention are adapted to supply the active ingredient to the oral cavity. The active may be absorbed across the sublingual mucosa for systemic distribution.

A variety of formulations are known which are suitable for delivering other active ingredients for absorption from the oral cavity. Such formulations may be useful in the present invention. Among them are intrabuccally disintegrating solid formulations or preparations which comprise the active ingredient, a sugar comprising lactose and/or mannitol and 0.12 to 1.2 w/w %, based on the solid components, of agar and which has a density of 400 mg/ml to 1,000 mg/ml and have a sufficient strength for handling, which in practice may mean sufficient strength to withstand removal from a blister packaging without disintegrating. Such formulations, and how to make them, are disclosed in U.S. Pat. No. 5,466,464, to which reference is made for further details.

In this embodiment of the invention, the sugar may be used in the formulation in an amount of at least 50 w/w %, preferably 80 w/w % or more, more preferably 90 w/w % or more, based on the total solid components, although it may vary depending on the quality and the quantity of the active ingredient to be used.

Though types of agar are not particularly limited, those listed in the Japanese Pharmacopoeia may be used preferably. Examples of the listed agar include agar powders PS-7 and PS-8 (manufactured by Ina Shokuhin).

Agar may be used in an amount from 0.12 to 1.2 w/w %, preferably from 0.2 to 0.4 w/w %, based on the solid components.

In order to produce a formulation in accordance with this embodiment of the present invention, a sugar comprising lactose and/or mannitol is suspended in an aqueous agar solution, filled with a mould, solidified into a jelly-like form and then dried. The aqueous agar solution may have a concentration of from 0.3 to 2.0%, preferably from 0.3 to 0.8%. The aqueous agar solution may be used in such an amount that the blending ratio of agar based on the solid components becomes 0.12 to 1.2 w/w %, but preferably 40 to 60 w/w % of agar solution based on the solid components.

Other formulations known for delivering active ingredients for absorption from the oral cavity are the dosage forms disclosed in U.S. Pat. Nos. 6,024,981 and 6,221,392. They are hard, compressed, rapidly dissolvable dosage forms adapted for direct oral dosing comprising: an active ingredient and a matrix including a non-direct compression filter and a lubricant, said dosage form being adapted to rapidly dissolve in the mouth of a patient and thereby liberate said active ingredient, and having a friability of about 2% or less when tested according to the U.S.P., said dosage form optionally having a hardness of at least about 15 Newtons (N), preferably from 15-50 N. U.S. Pat. Nos. 6,024,981 and 6,221,392 disclose further details and characteristics of these dosage forms and how to make them.

Preferably, dosage forms in accordance with this embodiment of the invention dissolve in about 90 seconds or less (preferably 60 seconds or less and most preferably 45 seconds or less) in the patient's mouth. It is also often desirable that the dosage form include at least one particle. The particle would be the active ingredient and a protective material. These particles can include rapid release particles and or sustained release particles.

In a particularly preferred formulation in accordance with this embodiment of the present invention there is provided a hard, compressed, rapidly dissolving tablet adapted for direct oral dosing. The tablet includes particles made of an active ingredient and a protective material. These particles are provided in an amount of between about 0.01 and about 75% by weight based on the weight of the tablet. The tablet also includes a matrix made from a non-direct compression filler, a wicking agent, and a hydrophobic lubricant. The tablet matrix comprises at least about 60% rapidly water soluble ingredients based on the total weight of the matrix material. The tablet has a hardness of between about 15 and about 50 Newtons, a friability of less than 2% when measured by U.S.P. and is adapted to dissolve spontaneously in the mouth of a patient in less than about 60 seconds and thereby liberate said particles and be capable of being stored in bulk.

A very find grained or powdered sugar known as a non-direct compression sugar may be used as a filler in the matrix of this embodiment the present invention. This material, in part because of its chemical composition and in part because of its fine particle size, will dissolve readily in the mouth in a matter of seconds once it is wetted by saliva. Not only does this mean that it can contribute to the speed at which the dosage form will dissolve, it also means that while the patient is holding the dissolving dosage form in his or her mouth, the filler will not contribute a "gritty" or "sandy" texture thus adversely affecting the organoleptic sensation of taking the dosage form. In contrast, direct compression versions of the same sugar are usually granulated and treated to make them larger and better for compaction. While these sugars are water soluble, they may not be solubilised quickly enough. As a result, they can contribute to the gritty or sandy texture of the dosage form as it dissolves. Dissolution time in the mouth can be measured by observing the dissolution time of the tablet in water at about 37° C. The tablet is immersed in the water without forcible agitation or with minimal agitation. The dissolution time is the time from immersion to substantially complete dissolution of the rapidly water soluble ingredients of the tablet as determined by visual observation.

Particularly preferred fillers, in accordance with the present invention are non-direct compression sugars and sugar alcohols which meet the specifications discussed above. Such sugars and sugar alcohols include, without limitation, dextrose, mannitol, sorbitol, lactose and sucrose. Of course, dextrose, for example, can exist as either a direct compression sugar, i.e., a sugar which has been modified to increase its compressibility, or a non-direct compression sugar.

Generally, the balance of the formulation can be matrix. Thus the percentage of filler can approach 100%. However, generally, the amount of non-direct compression filler useful in accordance with the present invention ranges from about 25 to about 95%, preferably between about 50 and about 95% and more preferably from about 60 to about 95%.

The amount of lubricant used can generally range from between about 1 to about 2.5% by weight, and more preferably between about 1.5 to about 2% by weight. Hydrophobic lubricants useful in accordance with the present invention include alkaline stearates, stearic acid mineral and vegetable oils, glyceryl behenate and sodium stearyl fumarate. Hydrophilic lubricants can also be used.

Protective materials useful in accordance with this embodiment of the present invention may include any of the polymers conventionally utilized in the formation of microparticles, matrix-type microparticles and microcapsules. Among these are cellulosic materials such as naturally occurring cellulose and synthetic cellulose derivatives; acrylic polymers and vinyl polymers. Other simple polymers include proteinaceous materials such as gelatin, polypeptides and natural and synthetic shellacs and waxes. Protective polymers may also include ethylcellulose, methylcellulose, carboxymethyl cellulose and acrylic resin material sold under the registered trade mark EUDRAGIT by Rhone Pharma GmbH of Weiterstadt, Germany.

In addition to the ingredients previously discussed, the matrix may also include wicking agents, non-effervescent disintegrants and effervescent disintegrants. Wicking agents are compositions which are capable of drawing water up into the dosage form. They help transport moisture into the interior of the dosage form. In that way the dosage form can dissolve from the inside, as well as from the outside.

Any chemical which can function to transport moisture as discussed above can be considered a wicking agent. Wicking agents include a number of traditional non-effervescent disintegration agents. These include, for example, microcrystalline cellulose (AVICEL PH 200, AVICEL PH 101), Ac-Di-Sol (Croscarmelose Sodium) and PVP-XL (a crosslinked polyvinylpyrrolidone); starches and modified starches, polymers, and gum such as Arabic and xanthan. Hydroxyalkyl cellulose such as hydroxymethylcellulose, hydroxypropylcellulose and hydroxyopropylmethylcellulose, as well as compounds such as carbopol may be used as well.

The conventional range of non-effervescent disintegrant agents used in conventional tablets can be as high as 20%. However, generally, the amount of disintegration agent used ranged from between about 2 and about 5%, according to the Handbook of Pharmaceutical Excipients.

In accordance with this embodiment of the present invention, the amount of wicking agents used may range from between 2 to about 12% and preferably from between 2 to about 5%.

It is also possible, of course, to include non-effervescent disintegrants which may not act to wick moisture, if desirable. In either event, it is preferable to use either rapidly water soluble, non-effervescent disintegrants or wicking agents and/or to minimize the use of generally non-water soluble wicking agents or non-effervescent disintegrants. Non-rapidly dissolvable, non-rapidly water soluble elements if used in sufficient quantity, can adversely affect the organoleptic properties of the tablets as they dissolve within the mouth and therefore should be minimized. Of course, wicking agents or non-effervescent disintegrants which are rapidly water soluble as discussed herein can be used in greater quantity and they will not add to the grittiness of the formulation during dissolution. Preferred wicking agents in accordance with the present invention include crosslinked PVP, although, the amounts of these must be controlled as they are not rapidly water soluble.

In addition, it may be desirable to use an effervescent couple, in combination with the other recited ingredients to improve the disintegration profile, the organoleptic properties of the material and the like. Preferably, the effervescent couple is provided in an amount of between about 0.5 and about 50%, and more preferably, between about 3 and about 15% by weight, based on the weight of the finished tablet. It is particularly preferred that sufficient effervescent material be provided such that the evolved gas is less than about 30 cm, upon exposure to an aqueous environment.

The term "effervescent couple" includes compounds which evolve gas. The preferred effervescent couple evolve gas by means of a chemical reaction which takes place upon exposure of the effervescent disintegration couple to water and/or to saliva in the mouth. This reaction is most often the result of the reaction of a soluble acid source and an alkali monohydrogencarbonate or other carbonate source. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, malic, fumaric, adipic, and succinics. Carbonate sources include dry sold carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

In the case of the orally dissolvable tablets in accordance with the present invention, it is preferred that both the amount and the type of disintegration agent, either effervescent or non-effervescent, and the combination thereof be provided sufficient in a controlled amount such that the tablet provides a pleasant organoleptic sensation in the mouth of the patient. In some instances, the patient should be able to perceive a distinct sensation of fizzing or bubbling as the tablet disintegrates in the mouth. In general, the total amount of wicking agents, non-effervescent disintegrants and effervescent disintegrants should range from 0-50%. However, it should be emphasized that the formulations of the present invention will dissolve rapidly and therefore, the need for disintegrating agents in minimal. As illustrated in the examples, appropriate hardness, friability and dissolution times can be obtained even without effervescent disintegrants or high quantities of wicking agents.

The use of a non-direct compression filler eliminates the need for many conventional processing steps such as granulation and/or the need to purchase more expensive pre-granulated, compressible fillers. At the same time, the resulting dosage form is a balance of performance and stability. It is robust enough to be conventionally produced using direct compression. It is robust enough to be stored or packaged in bulk. Yet, it rapidly dissolves in the mouth while minimizing the unpleasant feel of conventional disintegrating tablets to the extent possible.

Formulations in accordance with the embodiment of the invention may be made by a method including the steps of:

(a) forming a mixture including an active ingredient and a matrix including a non-direct compression filler and a lubricant;

(b) compressing the mixture to form a plurality of hard, compressed, rapidly disintegrable dosage forms including the active ingredient distributed in the orally dissolvable matrix; and optionally (c) storing the dosage forms in bulk prior to packaging. In a preferred embodiment, the dosage forms are then packaged in a lumen of a package such that there is at least one per package. In a preferred particularly preferred embodiment, the dosage forms are then packaged in a lumen of a package such that there more than one per package. Direct compression is the preferred method of forming the dosage forms.

Other formulations known for delivering active ingredients for absorption from the oral cavity are the dosage forms disclosed in U.S. Pat. No. 6,200,604, which comprise an orally administrable medicament in combination with an effervescent agent used as penetration enhancer to influence the permeability of the medicament across the buccal, sublingual, and gingival mucosa. In the content of the present invention, the medicament is desmopressin, which is administered in most embodiments across the sublingual mucosa. In the formulations of this embodiment of the invention, effervescent agents can be used alone or in combination with other penetration enhancers, which leads to an increase in the rate and extent of oral absorption of an active drug.

Formulations or dosage forms in accordance with this embodiment of the invention should include an amount of an effervescent agent effective to aid in penetration of the drug across the oral mucosa. Preferably, the effervescent is provided in an amount of between about 5% and about 95% by weight, based on the weight on the finished tablet, and more preferably in an amount of between about 30% and about 80% by weight. It is particularly preferred that sufficient effervescent material be provided such that the evolved gas is more than about 5 $cm^3$ but less than about 30 $cm^3$, upon exposure of the tablet to an aqueous environment.

The term "effervescent agent" includes compounds which evolve gas. The preferred effervescent agents evolve gas by means of a chemical reaction which takes place upon exposure of the effervescent agent (an effervescent couple) to water and/or to saliva in the mouth. This reaction is most often the result of the reaction of a soluble acid source and a source of carbon dioxide such as an alkaline carbonate or bicarbonate. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, amalic, fumeric, adipic, and succinies. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

The effervescent agent(s) useful in this embodiment of the present invention is not always based upon a reaction which forms carbon dioxide. Reactants which evolve oxygen or other gasses which are safe for human consumption are also considered within the scope. Where the effervescent agent includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

Such dosage forms may also include the amounts additional to that required for effervescence a pH adjusting substance. For drugs that are weakly acidic or weakly basic, the pH of the aqueous environment can influence the relative concentrations of the ionized and unionized forms of the drug present in solution according to the Henderson-Hasselbach equation. The pH solutions in which an effervescent couple has dissolved is slightly acidic due to the evolution of carbon dioxide. The pH of the local environment, e.g. saliva in immediate contact with the tablet and any drug that may have dissolved from it, may be adjusted by incorporating in the tablet a pH adjusting substances which permit the relative portions of the ionized and unionized forms of the drug to be controlled. In this way, the present dosage forms can be optimized for each specific drug. If the unionized drug is known or suspected to be absorbed through the cell membrane (transcellular absorption) it would be preferable to alter the pH of the local environment (within the limits tolerable to the subject) to a level that favours the unionized form of the drug. Conversely, if the ionized form is more readily dissolved the local environment should favour ionization.

The aqueous solubility of the drug should preferably not be compromised by the effervescent and pH adjusting substance, such that the dosage forms permit a sufficient concentration of the drug to be present in the unionized form. The percentage of the pH adjusting substance and/or effervescent should therefore be adjusted depending on the drug.

Suitable pH adjusting substance for use in the present invention include any weak acid or weak base in amounts additional to that required for the effervescence or, preferably, any buffer system that is not harmful to the oral mucosa. Suitable pH adjusting substance for use in the present invention include, but are not limited to, any of the acids or bases previously mentioned as effervescent compounds, disodium hydrogen phosphate, sodium dihydrogen phosphate and the equivalent potassium salt.

The dosage form of this embodiment of the invention preferably includes one or more other ingredients to enhance the absorption of the pharmaceutical ingredient across the oral mucosa and to improve the disintegration profile and the organoleptic properties of the dosage form. For example, the area of contact between the dosage form and the oral mucosa, and the residence time of the dosage form in the oral cavity can be improved by including a bioadhesive polymer in this drug delivery system. See, for example, Mechanistic Studies on Effervescent-Induced Permeability Enhancement by Jonathan Eichman (1997), which is incorporated by reference herein. Effervescence, due to its mucus stripping properties, would also enhance the residence time of the bioadhesive, thereby increasing the residence time for the drug absorption. Non-limiting examples of bioadhesives used in the present invention include, for example, Carbopol 934 P, Na CMC, Methocel, Polycarbophil (Noveon AA-1), HPMC, Na alginate, Na Hyaluronate and other natural or synthetic bioadhesives.

In addition to the effervescence-producing agents, a dosage form according to this embodiment of the present invention may also include suitable non-effervescent disintegration agents. Non-limiting examples of non-effervescent disintegration agents include: microcrystalline, cellulose, croscarmelose sodium, crospovidone, starches, corn starch, potato starch and modified starches thereof, sweeteners, clays, such as bentonite, alginates, gums such as agar, guar, locust bean, karaya, pectin and tragacanth. Disintegrants may comprise up to S about 20 weight percent and preferably between about 2 and about 10% of the total weight of the composition.

In addition to the particles in accordance with this embodiment of the present invention, the dosage forms may also include glidants, lubricants, binders, sweeteners, flavouring and colouring components. Any conventional sweetener or flavouring component may be used. Combinations of sweeteners, flavouring components, or sweeteners and flavouring components may likewise be used.

Examples of binders which can be used include acacia, tragacanth, gelatin, starch, cellulose materials such as methyl cellulose and sodium carboxy methyl cellulose, alginic acids and salts thereof, magnesium, aluminium silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Colouring agents may include titanium dioxide, and dyes suitable for food such as those known as F.D. & C. dyes and natural coloring agents such as grape skin extract, beet red powder, beta-carotene, annatto, carmine, turmeric, paprika, etc. The amount of colouring used may range from about 0.1 percent to about 3.5 weight percent of the total composition.

Flavours incorporated in the composition may be chosen from synthetic flavours oils and flavouring aromatics and/or natural oils, extracts from plants, leaves, flowers, fruits and so forth and combinations thereof. These may include cinnamon oil, oil of wintergreen, peppermint oils, clove oil, bay oil anise oil, eucalyptus, thyme oil, cedar leave oil, oil of nutmeg, oil of sage, oil of bitter almonds and cassia oil. Also useful as flavours are vanilla, citrus oil, including lemon, orange, grape, lime and grapefruit, and fruit essences, including apple, pear, peach, strawberry, raspberry, cherry, plum, pineapple, apricot and so forth. Flavours which have been found to be particularly useful include commercially available orange, grape, cherry and bubble gum flavours and mixtures thereof. The amount of flavouring may depend on a number of factors, including the organoleptic effect desired. Flavours may be present in an amount ranging from about 0.05 to about 3 percent by weight based upon the weight of the composition. Particularly preferred flavours are the grape and cherry flavours and the citrus flavours such as orange.

One aspect of the invention provides a solid, oral tablet dosage form suitable for sublingual administration. Excipient fillers can be used to facilitate tableting. The filler desirably will also assist in the rapid dissolution of the dosage form in the mouth. Non-limiting examples of suitable fillers include: mannitol, dextrose, lactose, sucrose, and calcium carbonate.

As described in U.S. Pat. No. 6,200,604, tablets can either be manufactured by direct compression, wet granulation or any other tablet manufacturing technique. The dosage form may be administered to a human or other mammalian subject by placing the dosage form in the subject's mouth and holding it in the mouth, beneath the tongue (for sublingual administration). The dosage form spontaneously begins to disintegrate due to the moisture in the mouth. The disintegration, particularly the effervescence, stimulates additional salivation which further enhances disintegration.

Although the above described formulations are within the scope of the present invention, the most preferred orodispersible solid pharmaceutical dosage forms according to the invention comprise a pharmaceutically active peptide and an open matrix network carrying desmopressin, the open matrix network being comprised of a water-soluble or water-dispersible carrier material that is inert towards desmopressin.

Pharmaceutical dosage forms comprising open matrix networks are known from GB-A-1548022, to which reference is made for further details. Pharmaceutical dosage forms of the invention can be rapidly disintegrated by water. By "rapidly disintegrated" is meant that the shaped articles are disintegrated in water within 10 seconds. Preferably the shaped article disintegrates (dissolves or disperses) within 5 seconds or less. The disintegration time is measured by a procedure analogous to the Disintegration Test for Tablets, B.P. 1973. The procedure is described in GB-A-1548022 and outlined below.

Apparatus

A glass or suitable plastic tube 80 to 100 mm long, with an internal diameter of about 28 mm and an external diameter of 30 to 31 mm, and fitted at the lower end, so as to form a basket, with a disc of rustproof wire gauze complying with the requirements for a No. 1.70 sieve.

A glass cylinder with a flat base and an internal diameter of about 45 mm containing water not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remains clear of the water.

Method

Place one shaped article in the basket and raise and lower it in such a manner that the complete up and down movement is repeated at a rate equivalent to thirty times a minute. The shaped articles are disintegrated when no particle remains above the gauze which would not readily pass through it. No such particle should remain after 10 seconds.

By the term "open matrix network" there is meant a network of water-soluble or water-dispersible carrier material having interstices dispersed throughout. The open matrix network of carrier material is of generally low density. For example the density may be within the range 10 to 200 mg/cc e.g. 10 to 100 mg/cc, preferably 30 to 60 mg/cc. The density of the shaped article may be affected by the amount of active ingredient, or any other ingredients, incorporated into the article and may be outside the above mentioned preferred limits for the density of the matrix network. The open matrix network which is similar in structure to a solid foam enables a liquid to enter the product through the interstices and permeate through the interior. Permeation by aqueous media exposes the carrier material of both the interior and exterior of the product to the action of the aqueous media whereby the network of carrier material is rapidly disintegrated. The open matrix structure is of a porous nature and enhances disintegration of the product as compared with ordinary solid shaped pharmaceutical dosage forms such as tablets, pills, capsules, suppositories and pessaries. Rapid disintegration results in rapid release of the active ingredient carried by the matrix.

The carrier material used in the product of the invention may be any water-soluble or water-dispersible material that is pharmacologically acceptable or inert to the chemical and which is capable of forming a rapidly disintegratable open matrix network. It is preferred to use water-soluble material as the carrier since this results in the most rapid disintegration of the matrix when the product is place in an aqueous medium. A particularly advantageous carrier may be formed from polypeptides such as gelatin, particularly gelatin which is particularly hydrolysed, e.g. by heating in water. For example, the gelatin may be partially hydrolysed by heating a solution of the gelatin in water, e.g. in an autoclave at about 120° C. for up to 2 hours, e.g. from about 5 minutes to about 1 hour, preferable from about 30 minutes to about 1 hour. The hydrolysed gelatin is preferably used at concentrations of about 1 to 6% weight/vol., most preferably at 2 to 4% e.g. about 3%.

Although mammalian derived gelatin may be used, it has an unpleasant taste and thus necessitates the use of sweeteners and flavours to mask the taste of the gelatin in addition to any sweeteners and flavours which may be required to mask the taste of the active ingredient. Moreover, the heating step necessary with the use of mammalian gelatin increases processing times and incurs heating costs thereby increasing the overall costs of the process. Therefore, the use of fish gelatin, especially non-gelling fish gelatin, is preferred, especially for desmopressin. Reference is made to WO-A-0061117 for further details.

Other carrier materials may be used in place of partially hydrolysed gelatin or fish gelatin, for example polysaccharides such as hydrolysed dextran, dextrin and alginates (e.g. sodium alginate) or mixtures of above mentioned carriers with each other or with other carrier materials such as polyvinyl alcohol, polyvinylpyrrolidine or acacia. Modified starch may also be used in place of gelatin, as described in WO-A-0044351, to which reference is made for further details. Additional carriers include water, lactose, starch, magnesium stearate, talc, plant oils, gums, alcohol, Vaseline (petroleum jelly), or the like.

Pharmaceutical dosage forms of the invention may be in the form of shaped articles. They may incorporate ingredients in addition to the active ingredient(s). For example the pharmaceutical dosage form of the present invention may incorporate pharmaceutically acceptable adjuvants. Such adjuvants include, for example, colouring agents, flavouring agents, preservations (e.g. bacteriostatic agents), and the like. U.S. Pat. No. 5,188,825 teaches that water soluble active agents should be bonded to an ion exchange resin to form a substantially water insoluble active agent/resin complex; although that teaching may be practiced here (for which reference to U.S. Pat. No. 5,188,825 is made for further details), it has been found in the development of the present invention that water soluble peptides such as desmopressin may be formulated in solid dosage forms of the invention without the need for bonding to an ion exchange resin. Such dosage forms may therefore be free of an ion exchange resin. For hydrophobic peptides, which desmopressin is not, a surfactant may be present, as taught in U.S. Pat. No. 5,827,541, to which reference is made for further details. For peptides with an unpleasant taste (which desmopressin does not have), a lipid such as a lecithin may be present to improve patient acceptability, as taught in U.S. Pat. No. 6,156,339, to which reference is made for further details. Other strategies for taste masking include conversion of a soluble salt to a less soluble salt or to the free base, as taught by U.S. Pat. Nos. 5,738,875 and 5,837,287, and the use of a process disclosed in U.S. Pat. No. 5,976,577 wherein, prior to freeze drying, a suspension of uncoated or coated coarse particles of the pharmaceutically active substance(s) in a carrier material is cooled to reduce the viscosity and minimize release of the active substance during processing, as well as beyond the point of disintegration of the form in the mouth, to minimize bad taste from the peptide; reference is made to the cited patents for further details.

For insoluble or poorly soluble peptides having a large particle size, xanthan gum may be present, particularly when the carrier is formed from gelatin, as the xanthan gum may act as a gelatin flocculating agent, as disclosed in U.S. Pat. No. 5,631,023, to which reference is made for further details.

As taught by WO-A-9323017 one or more amino acids having from about 2 to 12 carbon atoms may be present, when the matrix is selected from the group consisting of gelatin, pectin, soy fibre protein and mixtures thereof. In this formulation the preferred amino acid is glycine, while the preferred matrix forming agent is gelatin and/or pectin; in a particularly preferred embodiment, the dosage form additionally comprises mannitol. All excipients will be chosen to be pharmaceutically acceptable.

Pharmaceutical dosage forms of the present invention may be prepared by a process as described in GB-A-1548022, which comprises subliming solvent from a composition comprising the pharmaceutical substance and a solution of the carrier material in a solvent, the composition being in the solid state in a mould.

The sublimation is preferably carried out by freeze drying a composition comprising the active ingredient and a solution of the carrier material in a solvent. The composition may include additional ingredients, such as those mentioned above. The solvent is preferably water but it may contain a co-solvent (such as an alcohol e.g. tert-butyl alcohol) to improve the solubility of the chemical. The composition may also contain a surfactant e.g. Tween 80 (polyoxyethylene (20) sorbitan mono-oleate). The surfactant may help to prevent the freeze dried product sticking to the surface of the mould. It may also aid in the dispersion of the active ingredient.

The composition may contain a pH adjusting agent to adjust the pH of a solution from which the dosage form is prepared within the range of from 3 to 6, preferably from 3.5 to 5.5, and most preferably from 4 to 5, for example 4.5 or 4.8. Citric acid is a preferred pH adjusting agent, but others including hydrochloric acid, malic acid can be used. Such non-volatile pH adjusting agents will not be removed by the freeze drying or other sublimation process and so may be present in the final product.

The mould may comprise a series of cylindrical or other shape depressions in it, each of a size corresponding to the desired size of the shaped article. Alternatively, the size of the depression in the mould may be larger than the desired size of the article and after the contents have been freeze dried the product can be cut into the desired size (for example thin wafers).

However, as described in GB-A-2111423, the mould is preferably a depression in a sheet of filmic material. The filmic material may contain more than one depression. The filmic material may be similar to that employed in conventional blister packs which are used for packaging oral contraceptive tablets and like medicament forms. For example the filmic material may be made of thermoplastic material with the depressions formed by thermoforming. The preferred filmic material is a polyvinyl chloride film. Laminates of filmic material may also be used.

In one embodiment the mould comprises a metal plate (e.g. an aluminium plate) containing one or more depressions. In a preferred process using such a mould, the mould is cooled with a cooling medium (e.g. liquid nitrogen or solid carbon dioxide). When the mould is cooled a predetermined amount of water containing the carrier material, the active ingredient and any other desired ingredient is fed into the depression(s). When the contents of the depression(s) are frozen the mould is subjected to reduced pressure and, if desired, controlled application of heat to aid the sublimation. The pressure can be below about 4 mm. Hg; GB-A-1548022 teaches the employment of pressures of below 0.3 mm Hg, for example 0.1 to 0.2 mm is preferred. The freeze dried produces may be removed from the depressions in the mould and stored for future use, e.g. in airtight jars or other suitable storage containers. Alternatively, the freeze dried product may be enclosed by filmic material as described in GB-A-2111423.

A later developed process useful for making pharmaceutical dosage forms in accordance with the invention is described in GB-A-2111423, to which reference is made for further details. The process comprises filling a composition comprising a predetermined amount of active ingredient and a solution of partially hydrolysed gelatin into a mould, freezing the composition in the mould by passing gaseous cooling medium over the mould and then subliming solvent from the frozen composition so as to produce a network of-partially hydrolysed gelatin carrying the active ingredient.

In order to help ensure an even thickness of product, the side wall or walls of the mould may diverging outwards from the base and making an angle with the vertical of at least 5° at the surface of the composition, as described in GB-A-2119246 to which reference is made for further details.

Alternatively or in addition, pharmaceutical dosage forms of the present invention may be prepared by a process as described in GB-A-2114440 which comprises freezing a composition comprising a solution in a first solvent of a water-soluble or water dispersible carrier material that is inert towards the active ingredient, subliming the first solvent from the frozen composition so as to produce a product having a network of carrier material, adding to said product a solution or suspension of a second non-aqueous solvent containing a predetermined amount of the active ingredient and allowing or causing the second solvent to evaporate. Reference is made to GB-A-2114440 for further details.

Alternatively or in addition, pharmaceutical dosage forms of the present invention may be prepared by a process as described in GB-A-2111184, which comprises introducing the liquid medium in the form of droplets beneath the surface of a cooling liquid which is maintained at a temperature lower than the freezing point of the liquid medium, the cooling liquid being immiscible with, and inert with respect to, the liquid medium and having a density greater than that of both the liquid medium and the resulting frozen particles such as the liquid droplets float upwards in the cooling liquid towards the surface thereof, they are frozen to form spherical particles. The frozen spherical particles can be collected at or near the upper surface of the cooling liquid. Reference is made to GB-A-2111184 for further details.

Dosage forms in accordance with the invention have improved bioavailability. They are intended to be taken orally, and are highly suitable for that purpose. They disperse rapidly in the mouth, and may for example be placed under the tongue (sub-lingually).

According to a second aspect of the invention, there is provided a dosage form as described above for use in medicine, particularly, for voiding postponement, incontinence, primary nocturnal enuresis (PNE), nocturia and central diabetes insipidus.

The invention provides a method of postponing voiding, treating or preventing incontinence, primary nocturnal enuresis (PNE), nocturia and/or central diabetes insipidus, the method comprising administering an effective and generally non-toxic amount of desmopressin to a subject across the sublingual mucosa, for example in a dosage form as described above. Any other disease or condition treatable or preventable by desmopressin may similarly be addressed by means of invention. The invention therefore extends to the use of desmopressin in the manufacture of a sublingually absorbable pharmaceutical formulation. The invention also extends to a pack comprising a sublingually absorbable pharmaceutical dosage form of desmopressin together with instructions to place the dosage form under a patient's tongue.

Encompassed within the invention is also a method for preparing a packaged dosage form of desmopressin, the method comprising bringing into association a sublingually absorbable pharmaceutical dosage form of desmopressin and instructions to place the dosage form under a patient's tongue. The instructions may for example be printed on packaging encompassing the dosage form when sold or dispensed, or may be on a product information leaflet or insert within the packaging.

Other peptides apart from desmopressin are formulatable in the formulations described above. The invention therefore extends to a pharmaceutical dosage form of a pharmaceutically active peptide adapted for oral absorption.

According to a further aspect of the invention, there is provided a solid pharmaceutical dosage form, for example for oral administration, the dosage form comprising a pharmaceutically active peptide and an open matrix network carrying the peptide, the open matrix network being comprised of a water-soluble or water-dispersible carrier material that is inert towards the peptide.

Although oral vaccines made from fast dissolving dosage forms are known from WO-A-9921579, there is no disclosure of pharmaceutically active peptides retaining their activity after administration. The experimental work in WO-A-9921579 merely shows the presence in saliva of IgA antibodies to tetanus toxoid following the administration of tetanus toxoid by means of an adjuvanted fast dissolving dosage vaccine formulation. Formulations of the present invention are not vaccines and do not include adjuvants.

Pharmaceutical dosage forms of this aspect of the invention contain a pharmaceutically active peptide. Such peptides may be directly active per se or they may have one or more active metabolites, i.e. they may be prodrugs for the primary or true active principle. The peptides may have for example from 2 to 20, preferably from 5 to 15, amino acid residues (at least some of which may be D-isomer, although L-isomers will generally be predominant). The peptides may be linear, branched or cyclic, and may include natural residues or substituents or residues or substituents not found in natural peptides or proteins either commonly or al all. Pharmaceutically acceptable salts, simple adducts and tautomers are included where appropriate.

Examples of peptides usefully formulated by means of the invention include somatostatin and its analogues including Cyclo(MeAla-Tyr-$_D$-Trp-Lys-Val-Phe) and Cyclo(Asn-Phe-Phe-$_D$-Trp-$_D$-Lys-Thr-Phe-GABA), enkephalins including Met$^5$-enkephalin and Leu$^5$-enkephalin, oxytocin analogues such as atosiban (1-deamino-2-$_D$-Tyr-(OEt)-4-Thr-8-Om-oxytocin), GnRH analogues such as triptorelin (6-$_D$-Trp-GnRH), leuprolide ([$_D$-Leu$^6$, Pro$^8$-NHEt]-GnRH), degarelix (Ac-$_D$-2Nal-$_D$-4Cpa-$_D$-3Pal-Ser-4Aph(L-Hydroorotyl)-$_D$-4Aph(Cbm)-Leu-Ilys-Pro-$_D$-Ala-NH$_2$, where 2Nal is 2-naphthylalanine, 4Cpa is 4-chlorophenylalanine, 3Pal is 3-pyridylalanine, ILys is N(8)-isopropyllysine, 4Aph is 4-aminophenylalanine and Cbm is the carbamoyl group) and other GnRH antagonists disclosed in U.S. Pat. Nos. 5,925,730 and 4,072,668, and vasopressin analogues such as desmopressin. It is particularly preferred to formulate by means of the invention agonists of naturally active peptides, such as those described above, since agonists may be active at lower doses than antagonists Dosage will be as determined by the physician or clinician, depending on the nature of the peptide, the nature of the disease or condition being treated or prevented, and other factors.

The invention extends to the use of a peptide in the manufacture of a dosage form as described above for treating or preventing a disease or condition which is treatable or preventable by a peptide.

The invention also provides a method of preventing a disease or condition which is treatable or preventable by a peptide, the method comprising administering an effective and generally non-toxic amount of the peptide to a subject in a dosage form as described above.

Low Dosage Analysis and Applications

As indicated above, doses and plasma/plasma/serum concentrations of desmopressin which are from 5 to 40% of the current recommended doses and resulting plasma/plasma/serum levels are therapeutically effective and in some cases safer for certain disease conditions such as CDI, PNE, and additional clinical indications requiring pharmacological concentration of the urine.

Clinical observations in adult males and females treated with desmopressin for a condition known as nocturia (which results in frequent night time urination) suggested that lower dosages of desmopressin would be desirable. In this patient population, standard intranasal and oral doses of desmopressin produced an unexpectedly high incidence of hyponatremia, a condition in which plasma/plasma/serum sodium falls to abnormally low levels. Hyponatremia can result in seizures, cardiac arrhythmias, cerebral edema and death. The oral doses of desmopressin were in the 100 to 400 mcg range and the intranasal doses were in the 10 to 20 mcg range. While these doses decreased the incidence of nocturia, the hyponatremia suggested that the doses were unnecessarily high resulting in an excessive duration of pharmacodynamic effect on urine concentration with consequent overhydration and dilutional lowering of plasma/plasma/serum sodium. Lower doses of desmopressin would produce adequate but not excessive antidiuresis in terms of the magnitude and duration of action.

In accordance with the present invention, plasma/plasma/serum desmopressin concentrations following administration of the pharmaceutical composition of the invention preferably range from about 0.1 pg/mL to about 10.0 pg/mL, and more preferably from about 0.5 pg/mL to about 5.0 pg/mL. These amounts and ranges of desmopressin may be administered by any method known in the art, including, without limitation, intravenous (bolus, infusion); subcutaneous (bolus, infusion, depot); intranasal; transmucosal (buccal and sublingual, e.g., orodispersible tablets, wafers, film, and effervescent formulations; conjunctival (eyedrops); rectal (suppository, enema)); transdermal (passive via patch, gel, cream, ointment or iontophoretic); or intradermal (bolus, infusion, depot) as outlined below. Additionally, pharmaceutical compositions that contain desmopressin in an amount that provide the above plasma/plasma/serum desmopressin levels may be prepared by the above methods and using the above carriers, or any other method known in the art.

The dose ranges of desmopressin outlined above can produce appropriate antidiuretic effect when administered by various routes as summarized in the examples below:

| Route of Administration | Effective Daily Dose Range |
|---|---|
| Intravenous (bolus and infusion) | 0.5 ng-2000 ng |
| Subcutaneous (bolus, infusion, depot) | 0.5 ng-2000 ng |
| Intranasal | 0.1 mcg-20 mcg |
| Transmucosal including buccal and sublingual (orodispersible tablets, wafers, film and effervescent formulations), conjunctival (eyedrops), rectal (suppository, enema) | 0.1 mcg-20 mcg |
| Transdermal (passive via patch, gel, cream, ointment or iontophoretic) | 0.05 mcg-10 mcg |
| Intradermal (bolus, infusion, depot) | 0.05 mcg-10 mcg |

Administration of low dosages of desmopressin can be an effective treatment regimen for clinical indications such as treatment of central diabetes insipidus, prevention of primary nocturnal enuresis, prevention of nocturia, treatment of clinical disorders associated with nocturia including but not limited to sleep disturbances, prevention of incontinence (stress, urge, and the like), and voiding postponement during waking hours.

Specific formulations of desmopressin may also be created which enhance absorption and increase its systemic bioavailability. These formulations can result in incremental pharmacological effects at each point along the dose response curve, thus amplifying the activity of even low doses of desmopressin.

EXAMPLES

The present invention is further described in detail by means of the following Examples. All parts and percentages are by weight unless explicitly stated otherwise.

Example 1

200 µg Desmopressin Orodispersible Dosage Form

Spray-dried fish gelatin (4 g) and mannitol (3 g) are added to a glass beaker. Purified water (93 g) is then added and solution effected by stirring using a magnetic follower. The pH is checked and adjusted to 4.8 with citric acid as necessary. A Gilson pipette can then be used to deliver 500 mg of this solution into each one of a series of pre-formed blister pockets having a pocket diameter of about 16 mm. The blister laminate may comprise PVC coated with PVdC. The dosed units are then frozen at a temperature of −110° C. in a freeze tunnel with a residence time of 3.2 minutes and the frozen units are then held in an upright freezer for a time greater than 1.5 hours at a temperature of −25° C. (±5° C.). The units are then freeze-dried overnight with an initial shelf temperature of 10° C. rising to +20° C. at a pressure of 0.5 mbar. The units can be checked for moisture prior to unloading by the drying trace and by the pressurized moisture check.

In this way, following the general procedure given in Example 1 of WO-A-0061117, a desmopressin orodispersible dosage form is prepared using the following ingredients per unit dosage form:

| | |
|---|---|
| Desmopressin (PolyPeptide Laboratories, Sweden) | 200 µg |
| Mannitol EP/USP (Roquette, Mannitol 35) | 15 mg |
| Fish gelatin USNF/EP | 20 mg |
| Citric acid (if necessary) (pH adjusting agent) | q.s. to pH 4.8 |
| Purified water | (Removed during processing) |

Example 2

400 µg Desmopressin Orodispersible Dosage Form

The procedure of Example 1 herein is followed, except that the amount of desmopressin per unit dosage form was 400 µg.

Example 3

800 µg Desmopressin Orodispersible Dosage Form

The procedure of Example 1 herein is followed, except that the amount of desmopressin per unit dosage form was 800 µg.

Example 4

200 µg Desmopressin Orodispersible Dosage Form

Following the general procedure given in Example 1 of WO-A-0061117, a desmopressin dosage form orodispersible dosage form was prepared using the following ingredients per unit dosage form:

| | |
|---|---|
| Desmopressin (PolyPeptide Laboratories, Sweden) | 200 µg |
| Mannitol EP/USP (Roquette, Mannitol 35) | 6 mg |
| Fish gelatin USNF/EP | 10 mg |
| Citric acid (if necessary) (pH adjusting agent) | q.s. to pH 4.8 |
| Purified water | (Removed during processing) |

Example 5

400 µg Desmopressin Orodispersible Dosage Form

The procedure of Example 4 herein was followed, except that the amount of desmopressin per unit dosage form was 400 µg.

Example 6

800 µg Desmopressin Orodispersible Dosage Form

The procedure of Example 4 herein was followed, except that the amount of desmopressin per unit dosage form was 800 µg.

Comparative Example 1

Desmopressin i.v. Solution

An injectable preparation of desmopressin was conventionally prepared using the following ingredients:

| | |
|---|---|
| Desmopressin (PolyPeptide Laboratories, Sweden) | 4 mg |
| Sodium chloride | 9 mg |

-continued

| | |
|---|---|
| (National Corporation of Swedish Pharmacies, Sweden) | |
| Hydrochloric acid (1N) (Merck, Germany) | q.s. to pH 4 |
| Water for injection | q.s. to 1 ml |

Comparative Example 2

200 µg Desmopressin Conventional Tablet

Using a conventional wet granulation process, tablets containing the following ingredients were prepared:

| | |
|---|---|
| Desmopressin (PolyPeptide Laboratories, Sweden) | 200 µg |
| Lactose (Pharmatose 150M, DMV, The Netherlands) | 120 mg |
| Potato starch (Lyckeby AB, Sweden) | 77 mg |
| PVP (Kollidon 25, BASF, Germany) | 1.8 mg |
| Magnesium stearate (Peter Greven, Germany) | 1 mg |
| Granulation Liquid (water, ethanol) | (Removed during processing) |

Comparative Example 3

100 µg Desmopressin Conventional Tablet

The procedure of Comparative Example 2 was followed, except that the amount of desmopressin was 100 µg per tablet.

Example 7

Bioavailability Of Desmopressin Administered in Accordance with Examples 4 to 6

Study Design

Twenty-four healthy non-smoking male volunteers were enrolled in the present study. The study was designed as a one-centre, open-labelled, randomized, balanced, 4-way cross-over phase I study. Each subject was, in a randomized order, administered sublingually desmopressin as a 200 µg, 400 µg and 800 µg orodispersible dosage form (Examples 4, 5 and 6, respectively) and 2 µg as an i.v. bolus dose (Comparative Example 1). Between the doses there was a washout period of 72 hours. In order to standardize the buccal mucosa before administration of the orodispersible tablet, the subjects were asked to avoid foods, chewing gum etc. Subjects were allowed to brush their teeth in the morning before dosing, but without toothpaste.

Blood Samples

Blood samples for plasma concentration of desmopressin were collected according to the following schedule: pre-dose and 15, 30 and 45 min and at 1, 1.5, 2, 3, 4, 6, 8, 10, 12 and 24 hours post-dosing. After intravenous administration additional blood samples were collected 5 and 10 minutes post-dosing.

Assay

The concentration of desmopressin in plasma was determined by a validated RIA method.

Pharmacokinetic Analysis

The concentration of desmopressin in plasma was analyzed for the individual volunteer in each administration group, by use of non-compartmental methods using the commercially available software WinNonlin™ Pro, ver. 3.2 (Pharsight Corporation, US). A plasma concentration value below limit of quantitation (LOQ) followed by values above LOQ was set at 'LOQ/2' for the NCA analysis and for the descriptive statistics on concentrations. Values below LOQ not followed by values above the LOQ are excluded from the NCA analysis, and set to zero in the descriptive statistics on concentrations.

Results of Pharmacokinetic Analysis

After i.v. administration the mean volume of distribution at steady state (Vss) was 29.7 Dm$^3$. The mean clearance was calculated to be 8.5 dm$^3$/hr and the mean elimination half-life was determined to be 2.8 hours. After oral administration of desmopressin maximum plasma concentrations were observed at 0.5-2.0 hours after dosing. The maximum plasma concentration was 14.25, 30.21 and 65.25 pg/ml after an oral dose of 200, 400 and 800 µg, respectively. After reaching the maximum value desmopressin was eliminated with a mean elimination half-life in the range of 2.8-3.0 hours. The bioavailability was determined to be 0.30% with at 95% confidence interval of 0.23-0.38%.

The pharmacokinetics of desmopressin is linear, when administered as the orodispersible dosage form of Example 4, 5 or 6.

Comparative Example 4

Bioavailability of Desmopressin Administered in Accordance with Comparative Examples 2 and 3

Thirty-six healthy male volunteers (Caucasian, Black and Hispanic) were enrolled in this study, which was designed as an open label, single dose, 3-way crossover study. Each subject was, in a randomized order, administered 200 µg desmopressin as a single 200 µg tablet (Comparative Example 2), 200 µg desmopressin as two 100 µg tablets (Comparative Example 3) and 2 pg as an i.v. bolus dose (Comparative Example 1).

After i.v. administration the mean elimination half-life was determined to be 2.24 hours. After oral administration of desmopressin maximum plasma concentrations were observed at 1.06 hours (2×100 µg) or 1.05 hours (1×200 µg) after dosing. The maximum plasma concentration was 13.2 and 15.0 pg/ml after an oral dose of 2×100 µg and 1×200 µg, respectively. The bioavailability was determined to be 0.13% (2×100 µg) or 0.16% (1×200 µg).

Example 8

Crossover Study Investigating the Antidiuretic Effect of Three Low Doses of Desmopressin The following Example describes a study showing the antidiuretic effect of three low doses of desmopressin administered via intravenous infusion for 2 hours in over-hydrated, healthy, non-smoking male and female volunteers. Briefly, an open-label, crossover study with 8 healthy, over-hydrated, non-smoking male and female volunteers, age 18-40. The subjects were dosed initially with 0.5 ng/kg dose, then with the 1.0 ng/kg dose and finally the 2.0 ng/kg dose. Pharmacodynamic and pharmacokinetic parameters were evaluated at each dose level. A washout period of two days (48 hours) was observed between dosing.

Eight subjects evaluated in this study, 5 males, and 3 females. Their weights in kilograms were: 85.9, 65, 80.9, 63.3, 72.5, 67.6, 63.5, and 54.5. The mean weight of the 8 subjects was 69.15 kg, which is very close to the standard 70 kg weight estimate upon which the doses and blood levels of desmopressin in this study are based. Subjects were over-hydrated on study day 1 (first day of dosing) by drinking a volume of water equal to 1.5% of body weight and maintained by replacing urine output with water ingestion. Desmopressin of 0.5, 1.0 and 2.0 ng/kg in 100 mL of sterile, physiological saline (0.9%), USP for injection, was used in the study. Three infusions of desmopressin (one at each of the above concentrations) was administered as an I.V. infusion at a constant rate, each 2 hours in duration on days 1, 3 and 5 of the study. Each subject remained in the clinic from one day prior to first dosing to one day after last dosing for a total of 7 days. The first dose was 0.5 ng/kg. Following the end of the desmopressin infusion, subjects voided every 20 minutes and were monitored until 3 consecutive urine collections measured a urine output level exceeding 10 mL/min. At this point over-hydration was discontinued. Urine osmolality was measured 20 minutes before the infusion, at baseline, and with every 20 minute urine collection up to 6 hours after the start of the infusion. Urine-specific gravity was also measured. Plasma/serum sodium and plasma/serum osmolality was measured prior to dosing and at 2, 4, and 6 hours after the start of the infusion. Blood samples for pharmacokinetic determinations were collected predose, 15, 30, and 45 minutes and 1, 1.5, 2, 3, 4, 6, 8 and 12 hours after the start of the infusion. This same procedure was followed for the 1.0 ng/kg and 2.0 ng/kg infusions. On day 6, approximately 24 hours after the third and last desmopressin infusion subjects had an exit physical examination with vital signs, blood and urine laboratory assessments.

Criteria for evaluation in the study included urine output over time, urine osmolality over time, urine-specific gravity over time, and plasma/plasma/serum osmolality and sodium over time. Statistical analysis on the above criteria was performed. The statistical analysis is descriptive and all statistical hypothesis testing was done for exploratory purposes. The following was investigated: duration of action, i.e., time from 'onset' to 'end' action was estimated for each subject using three different levels of osmolality as cut off (150 mOsm/kg, 200 mOsm/kg and 400 mOsm/kg). First, duration of action was defined as the time from onset of action (i.e., the first time after dose administration where urine osmolality was less than 150 mOsm/kg) to end of action (the first subsequent time where urine osmolality was less than 150 mOsm/kg and confirmed at the next interval unless the first subsequent time was the last observation point). The second and third estimation used 200 mOsm/kg and 400 mOsm/kg as cut off levels for 'onset' and 'end' of action, respectively. Subjects with no 'end' of action, with respect to the definition were censored at the time their urinary output returns to baseline (exceeds 10 mL/min) and/or the time where the over-hydration procedure stopped. The overall duration of action was estimated for each dose group using the nonparametric Kaplan-Meier method. The different approaches for estimating duration of action were expected to give lower and upper limits of the true probability, i.e., probability of desmopressin activity as a function of time. Furthermore, the duration of action was presented for each treatment group using the mean, SD, median, minimum and maximum values. The dose-response relationship between duration of action and dose was investigated using an appropriate linear or nonlinear model. Pharmacokinetic parameters were derived from the individual concentration versus time curves of desmopressin, i.e., AUC (area under the plasma concentration time curve to infinity), $C_{max}$ (maximum plasma concentration observed), $t_{max}$ (time of $C_{max}$ after dosing), CL (total systemic clearance), $V_z$ (volume of distribution during the terminal phase), $AUC_t$ (area under the plasma concentration time curve from time zero to time t), $\lambda_z$ (first order rate constant associated with the terminal (log-linear) portion of the plasma concentration time curve estimated via linear regression of the time vs. log of concentration) and $t_{1/2}$ (terminal half life).

Figure 2:
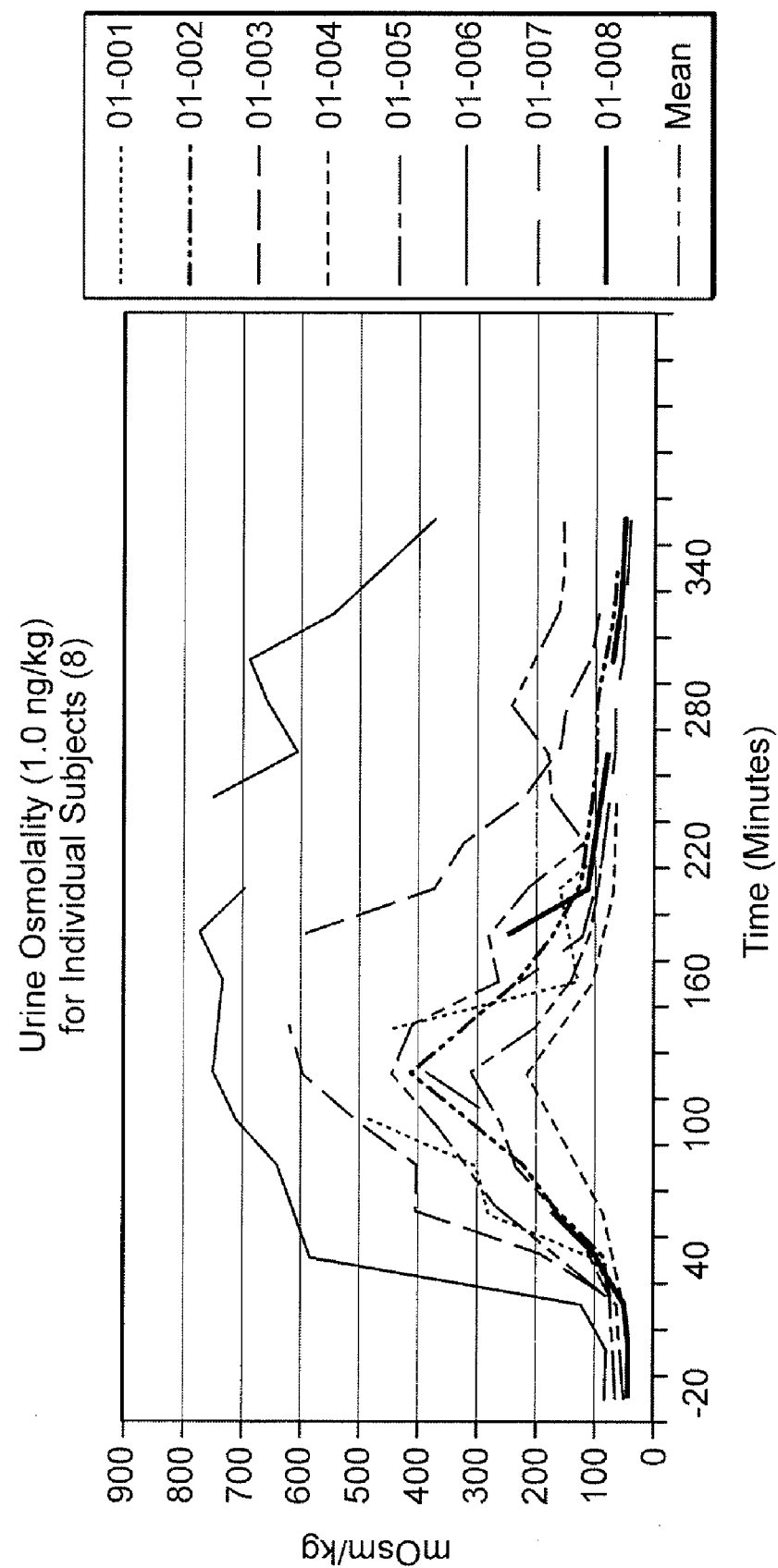
FIG. 2 shows urine osmolality for each subject as a result of administration of 1.0 ng/kg of desmopressin.
Figure 3:
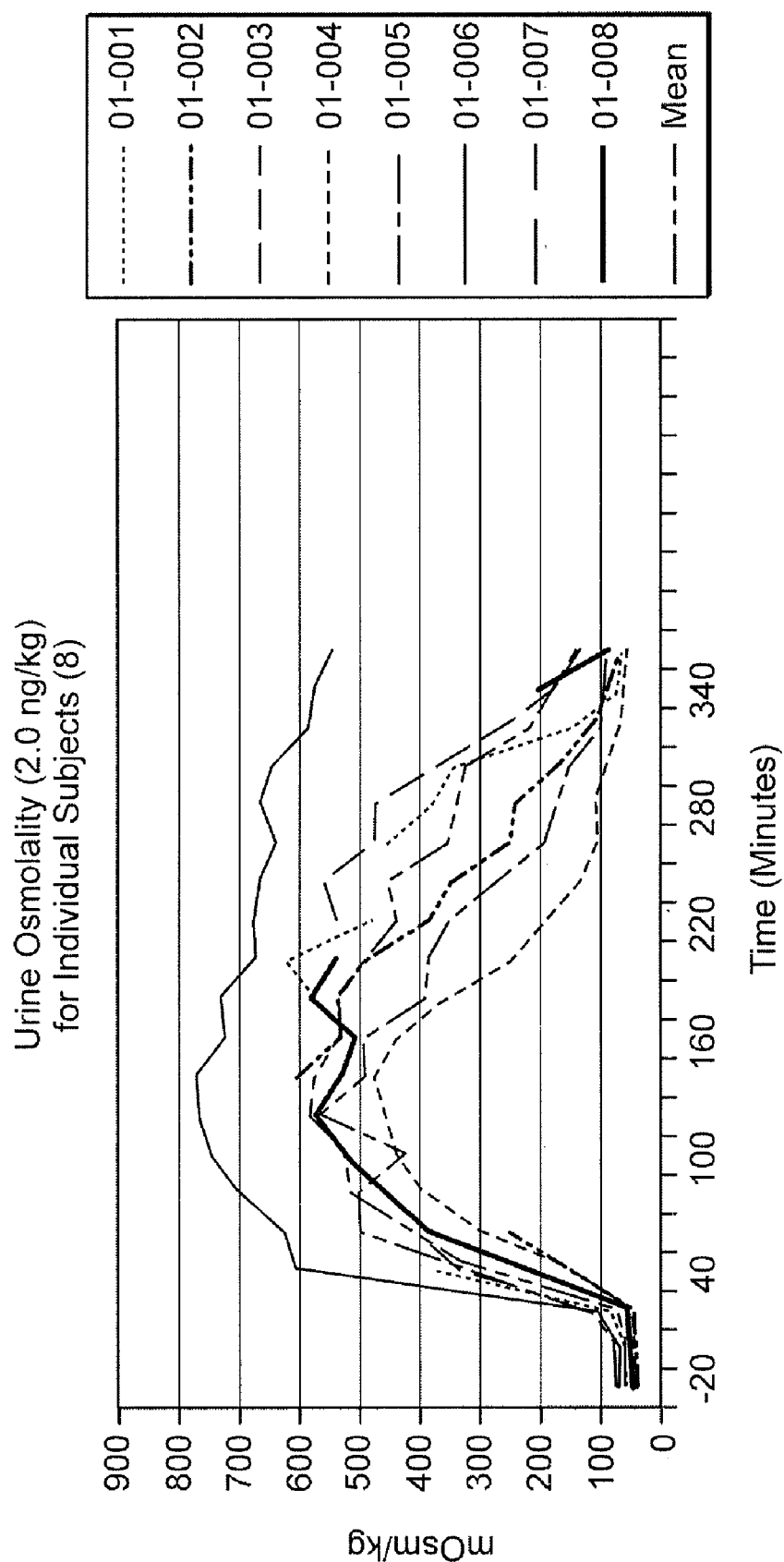
FIG. 3 shows urine osmolality for each subject as a result of administration of 2.0 ng/kg of desmopressin.
Figure 4:
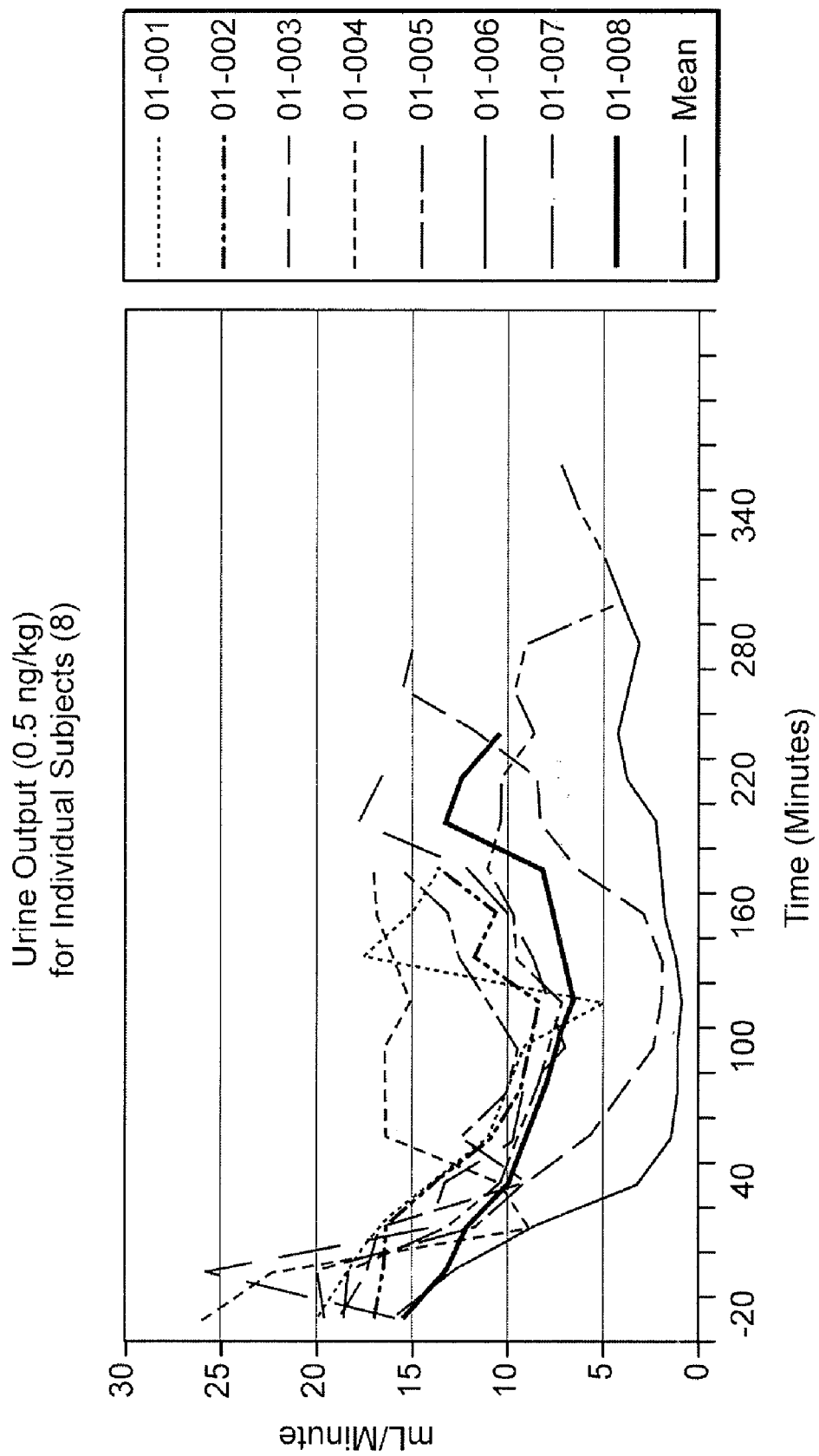
FIG. 4 shows urine output for each subject as a result of administration of 0.5 ng/kg of desmopressin.
Figure 5:
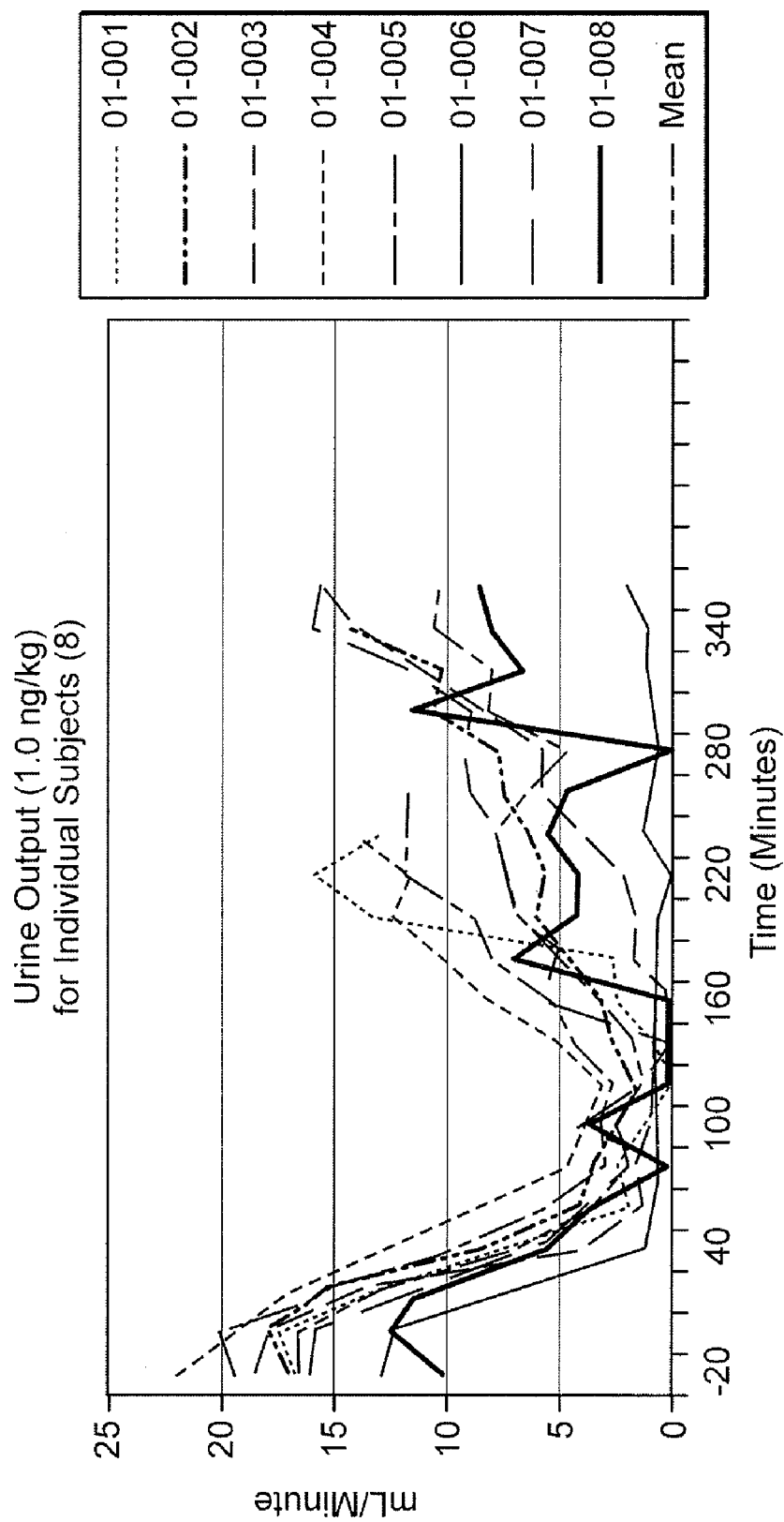
FIG. 5 shows urine output for each subject as a result of administration of 1.0 ng/kg of desmopressin.
Figure 6:
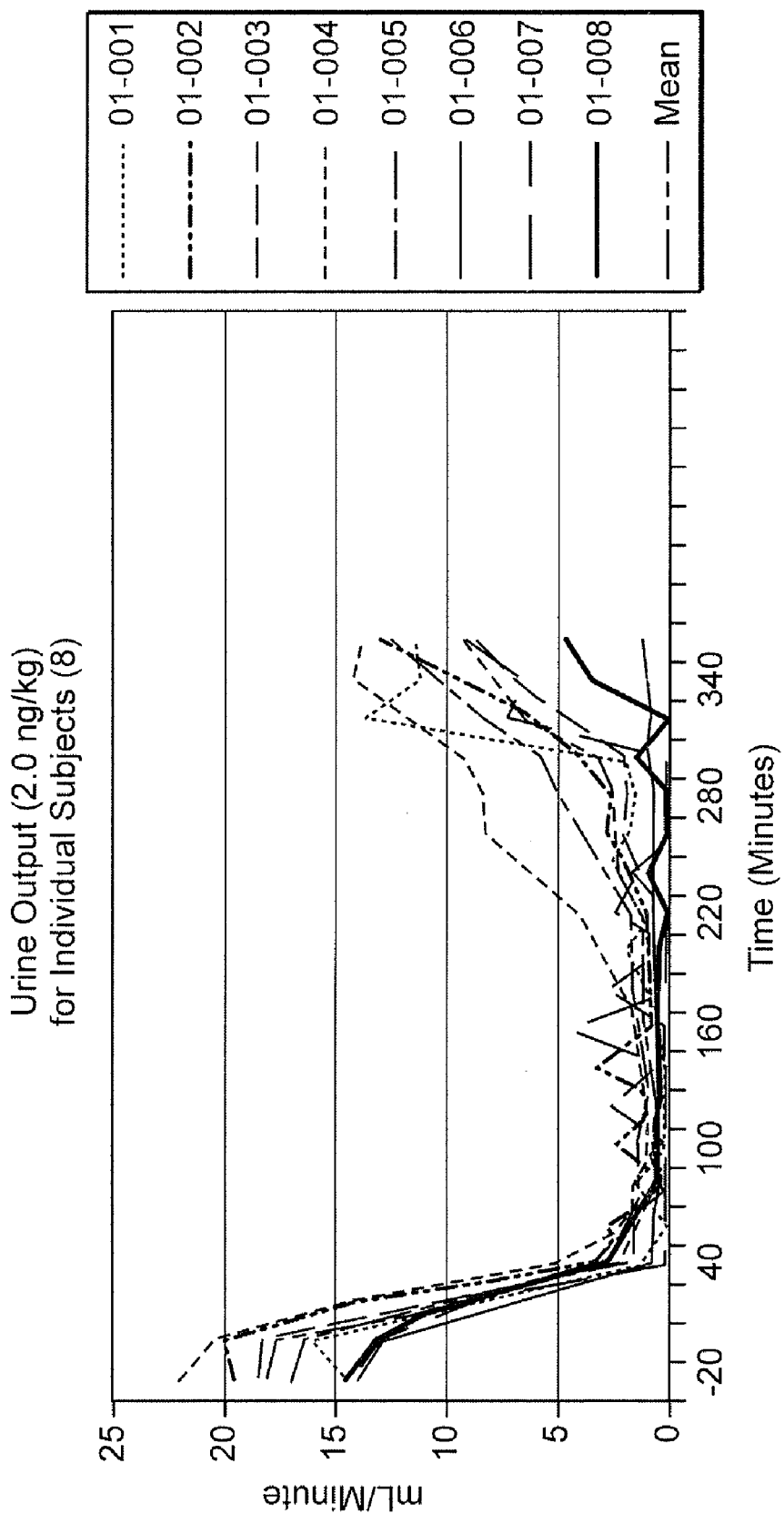
FIG. 6 shows urine output for each subject as a result of administration of 2.0 ng/kg of desmopressin.
Figure 7:
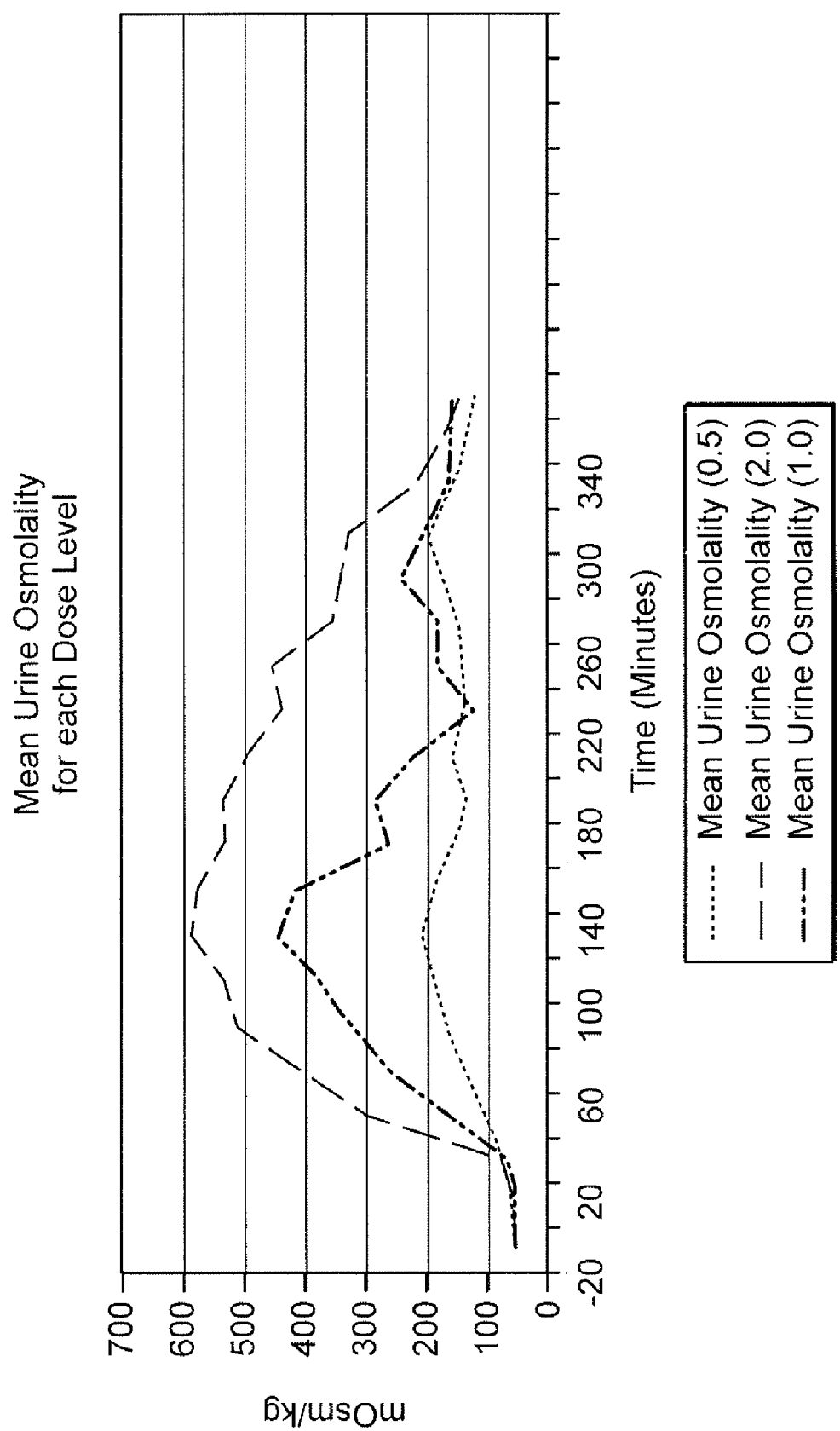
FIG. 7 shows mean urine osmolality resulting from administration of 0.5, 1.0, and 2.0 ng/kg desmopressin.
Figure 8:
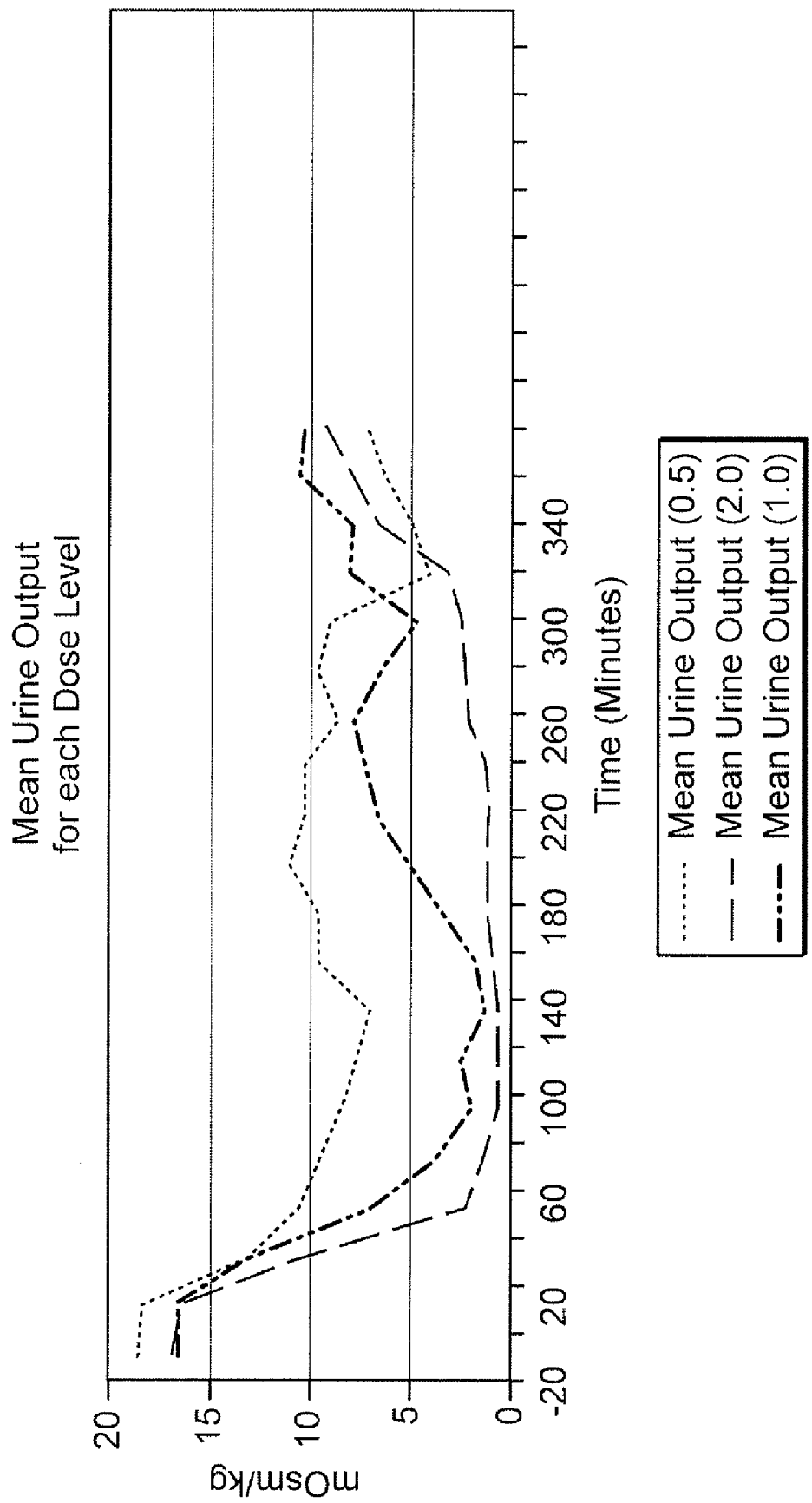
FIG. 8 shows urine output resulting from administration of 0.5, 1.0, and 2.0 ng/kg desmopressin.
Figure 9:
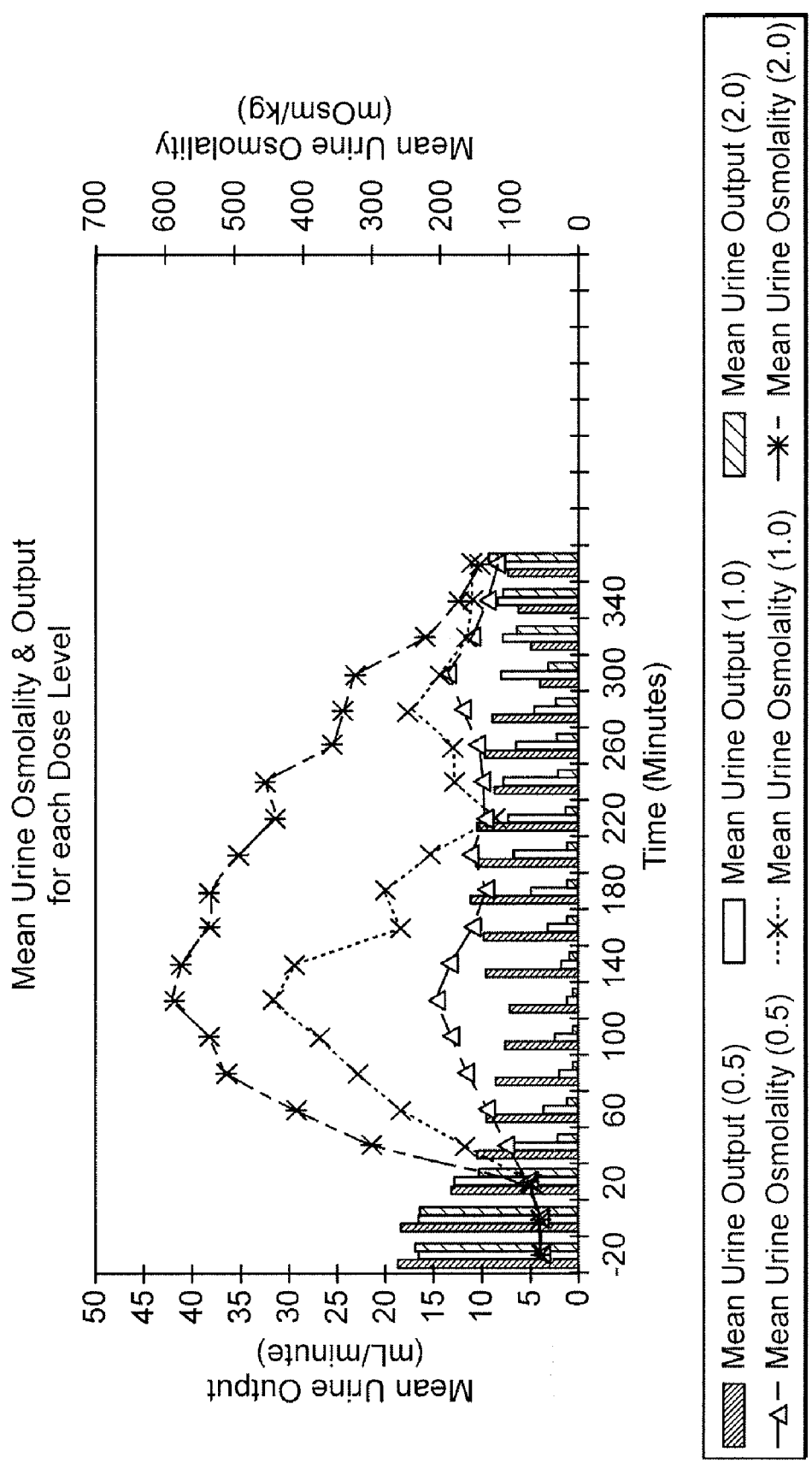
FIG. 9 shows mean urine osmolality and mean urine output resulting from administration of 0.5, 1.0, and 2.0 ng/kg desmopressin.

Summary of Results:

All three doses (I.V. infusions) of desmopressin produced a measurable, antidiuretic effects in terms of increased urine concentration (osmolality) and decreased urine output in a dose response fashion. The pharmacodynamic duration of antidiuretic effect also demonstrated a dose response curve with the lowest dose having the shortest duration of effect. The mean peak urine osmolality (mOsm/kg) occurred at the end of the 2 hour infusion for each dose level. Baseline mean urine osmolality was 55.8, 55.8 and 55.6 mOsm/kg for 0.5, 1.0, 2.0 ng/kg doses, respectively. Mean peak urine osmolality was 206.0, 444.7 and 587.2 mOsm/kg at 2 hours for the 0.5, 1.0 and 2.0 ng/kg doses, respectively. The mean nadir urine output (mL/min) also occurred at the end of the 2 hour infusion for each dose level. Baseline mean urine output was 18.6, 16.6 and 16.9 mL/min for the 0.5, 1.0 and 2.0 ng/kg doses, respectively. Mean nadir urine output was 7.1, 1.3, and 0.7 mL/min for the 0.5, 1.0 and 2.0 ng/kg doses, respectively. The duration of antidiuretic effect was approximately 180 minutes for the 0.5 ng/kg dose, 240 to 280 minutes for the 1.0 ng/kg dose and 360 minutes for the 2.0 ng/kg dose. The urine osmolality and output results for each subject and the means for each time period are described in Tables 1-6 and FIGS. 1-9.

TABLE 1

Urine Osmolality (0.5 ng/kg)

| Subject # | Time (Minutes) | | | | | | | | | |
|---|---|---|---|---|---|---|---|---|---|---|
| | −20 | 0 | 20 | 40 | 60 | 80 | 100 | 120 | 140 | 160 |
| 01-001 | 61 | 61 | 63 | 75 | 84 | 91 | 100 | 104 | 93 | 57 |
| 01-002 | 41 | 43 | 46 | 55 | 70 | 83 | 91 | 90 | 79 | 72 |
| 01-003 | 57 | 57 | 65 | 105 | 162 | 228 | 338 | 447 | 363 | 243 |
| 01-004 | 49 | 49 | 97 | 100 | 57 | 56 | 58 | 61 | 59 | 57 |
| 01-005 | 57 | 60 | 95 | 110 | 89 | 83 | 84 | 87 | 80 | 74 |
| 01-006 | 80 | 85 | 115 | 294 | 476 | 621 | 633 | 655 | 670 | 601 |
| 01-007 | 52 | 54 | 56 | 72 | 86 | 95 | 108 | 119 | 87 | 75 |
| 01-008 | 49 | 52 | 48 | 55 | 65 | 69 | 78 | 85 | 75 | 67 |
| Mean | 55.8 | 57.6 | 73.1 | 108.3 | 136.1 | 165.8 | 186.3 | 206.0 | 188.3 | 155.8 |

TABLE 1-continued

| | Urine Osmolality (0.5 ng/kg) | | | | | | | | | |
|---|---|---|---|---|---|---|---|---|---|---|
| | Time (Minutes) | | | | | | | | | |
| Subject # | 180 | 200 | 220 | 240 | 260 | 280 | 300 | 320 | 340 | 360 |
| 01-001 | 78 | * | * | * | * | * | * | * | * | * |
| 01-002 | 66 | * | * | * | * | * | * | * | * | * |
| 01-003 | 177 | 122 | 103 | 93 | 80 | 88 | * | * | * | * |
| 01-004 | 55 | * | * | * | * | * | * | * | * | * |
| 01-005 | 71 | * | * | * | * | * | * | * | * | * |
| 01-006 | 521 | 390 | 327 | 274 | 215 | 250 | 193 | 156 | 133 | 120 |
| 01-007 | 65 | 59 | 57 | * | * | * | * | * | * | * |
| 01-008 | 61 | 60 | 59 | 58 | * | * | * | * | * | * |
| Mean | 136.8 | 157.8 | 136.5 | 141.7 | 147.5 | 169.0 | 193.0 | 156.0 | 133.0 | 120.0 |

TABLE 2

| | Urine Osmolality (1.0 ng/kg) | | | | | | | | | |
|---|---|---|---|---|---|---|---|---|---|---|
| | Time (Minutes) | | | | | | | | | |
| Subject # | −20 | 0 | 20 | 40 | 60 | 80 | 100 | 120 | 140 | 160 |
| 01-001 | 58 | 59 | 65 | 108 | 281 | 305 | 480 | * | 435 | 132 |
| 01-002 | 46 | 44 | 53 | 91 | 168 | 222 | 315 | 414 | 324 | 230 |
| 01-003 | 48 | 51 | 60 | 178 | 406 | 402 | 506 | 595 | 618 | * |
| 01-004 | 48 | 49 | 52 | 68 | 92 | 135 | 180 | 219 | 156 | 105 |
| 01-005 | 68 | 68 | 73 | 106 | 166 | 235 | 260 | 312 | 204 | 142 |
| 01-006 | 82 | 82 | 124 | 585 | 614 | 638 | 708 | 747 | 736 | 733 |
| 01-007 | 47 | 47 | 53 | 100 | 175 | * | 267 | 381 | * | 228 |
| 01-008 | 49 | 52 | 57 | 100 | 173 | * | 288 | * | * | * |
| Mean | 55.8 | 56.5 | 67.1 | 167.0 | 259.4 | 322.8 | 375.5 | 444.7 | 412.2 | 261.7 |
| | Time (Minutes) | | | | | | | | | |
| Subject # | 180 | 200 | 220 | 240 | 260 | 280 | 300 | 320 | 340 | 360 |
| 01-001 | 150 | 160 | 71 | 60 | * | * | * | * | * | * |
| 01-002 | 171 | 127 | 116 | 104 | 99 | 98 | 82 | 68 | 62 | * |
| 01-003 | 588 | 374 | 322 | 221 | 162 | 148 | 111 | 96 | * | * |
| 01-004 | 85 | 71 | 71 | 67 | * | * | * | * | * | * |
| 01-005 | 109 | 94 | 88 | 83 | 75 | * | * | * | * | * |
| 01-006 | 771 | 694 | * | 747 | 606 | 655 | 687 | 546 | 458 | 374 |
| 01-007 | 122 | 96 | 86 | 81 | 69 | 69 | 57 | 53 | 47 | 44 |
| 01-008 | 251 | 114 | 96 | 90 | 80 | * | 73 | 61 | 55 | 51 |
| Mean | 280.9 | 216.3 | 121.4 | 181.6 | 181.8 | 242.5 | 202.0 | 164.8 | 155.5 | 156.3 |

TABLE 3

| | Urine Osmolality (2.0 ng/kg) | | | | | | | | | |
|---|---|---|---|---|---|---|---|---|---|---|
| | Time (Minutes) | | | | | | | | | |
| Subject # | −20 | 0 | 20 | 40 | 60 | 80 | 100 | 120 | 140 | 160 |
| 01-001 | 63 | 63 | 88 | 373 | * | 526 | * | * | 585 | * |
| 01-002 | 40 | 40 | 46 | 149 | 251 | * | 492 | * | 601 | 533 |
| 01-003 | 51 | 52 | 73 | 337 | 401 | * | * | 568 | * | * |
| 01-004 | 45 | 48 | 50 | 146 | 298 | 390 | 442 | 461 | 478 | 439 |
| 01-005 | 78 | 73 | 119 | 293 | 499 | 501 | 421 | 564 | 492 | 492 |
| 01-006 | 71 | 73 | 108 | 604 | 626 | 698 | 748 | 769 | 771 | 727 |
| 01-007 | 45 | 45 | 60 | * | * | * | * | * | * | 509 |
| 01-008 | 52 | 54 | 61 | 208 | 385 | 465 | 525 | 574 | 533 | 508 |
| Mean | 55.6 | 56.0 | 75.6 | 301.4 | 410.0 | 516.0 | 525.6 | 587.2 | 576.7 | 534.7 |
| | Time (Minutes) | | | | | | | | | |
| Subject # | 180 | 200 | 220 | 240 | 260 | 280 | 300 | 320 | 340 | 360 |
| 01-001 | 571 | 623 | 482 | * | 458 | 384 | 346 | 146 | 73 | 76 |
| 01-002 | 538 | 489 | 385 | 348 | 252 | 244 | 173 | 116 | 87 | 76 |
| 01-003 | 568 | * | 541 | 559 | 477 | 476 | 380 | 267 | 179 | 134 |
| 01-004 | 357 | 250 | 195 | 139 | 110 | 112 | 97 | 73 | 66 | 60 |

TABLE 3-continued

Urine Osmolality (2.0 ng/kg)

| 01-005 | 390 | 387 | 352 | 267 | 195 | 178 | 154 | 104 | 98 | 87 |
|---|---|---|---|---|---|---|---|---|---|---|
| 01-006 | 733 | 676 | 677 | 668 | 640 | 665 | 648 | 585 | 577 | 547 |
| 01-007 | * | * | * | 666 | * | * | * | 255 | 100 | 79 |
| 01-008 | 583 | 542 | * | 539 | * | * | 473 | * | 204 | 91 |
| Mean | 534.3 | 494.5 | 438.7 | 455.1 | 355.3 | 343.2 | 324.4 | 220.9 | 173.0 | 143.8 |

TABLE 4

Urine Output (0.5 ng/kg)

| Subject # | Time (Minutes) | | | | | | | | | |
|---|---|---|---|---|---|---|---|---|---|---|
| | −20 | 0 | 20 | 40 | 60 | 80 | 100 | 120 | 140 | 160 |
| 01-001 | 20 | 18.8 | 16.7 | 14 | 10.9 | 10 | 9.1 | 5 | 17.6 | 15 |
| 01-002 | 17 | 16.5 | 16.4 | 13.8 | 10.8 | 9.3 | 8.8 | 8.3 | 11.8 | 10.5 |
| 01-003 | 18.8 | 17.4 | 16.7 | 9 | 5.9 | 4.1 | 2.4 | 2 | 2 | 3 |
| 01-004 | 26 | 22.3 | 8.9 | 10.5 | 16.4 | 16.5 | 16.5 | 15.2 | 16 | 17 |
| 01-005 | 19.5 | 20 | 11.8 | 9 | 12.5 | 10 | 9.5 | 10.9 | 12.5 | 13 |
| 01-006 | 15.9 | 13 | 8.8 | 3.1 | 1.4 | 1.1 | 1.1 | 0.9 | 1.2 | 1.8 |
| 01-007 | 16.1 | 25.8 | 14 | 13.3 | 9.6 | 9.2 | 7 | 8 | 8.7 | 10 |
| 01-008 | 15.5 | 13.3 | 12.2 | 10 | 9.1 | 8.1 | 7.5 | 6.5 | 7.1 | 7.6 |
| Mean | 18.6 | 18.4 | 13.2 | 10.3 | 9.6 | 8.5 | 7.7 | 7.1 | 9.6 | 9.7 |

| Subject # | Time (Minutes) | | | | | | | | | |
|---|---|---|---|---|---|---|---|---|---|---|
| | 180 | 200 | 220 | 240 | 260 | 280 | 300 | 320 | 340 | 360 |
| 01-001 | 13.6 | * | * | * | * | * | * | * | * | * |
| 01-002 | 13.6 | * | * | * | * | * | * | * | * | * |
| 01-003 | 6.4 | 8.3 | 8.5 | 11.4 | 15.6 | 15 | * | * | * | * |
| 01-004 | 17.1 | * | * | * | * | * | * | * | * | * |
| 01-005 | 15.7 | * | * | * | * | * | * | * | * | * |
| 01-006 | 2 | 2.2 | 3.8 | 4.2 | 3.8 | 3.2 | 4.1 | 5 | 6.4 | 7.3 |
| 01-007 | 12.2 | 17.9 | 16.7 | * | * | * | * | * | * | * |
| 01-008 | 8.2 | 13.3 | 12.5 | 10.5 | * | * | * | * | * | * |
| Mean | 11.1 | 10.4 | 10.4 | 8.7 | 9.7 | 9.1 | 4.1 | 5.0 | 6.4 | 7.3 |

TABLE 5

Urine Output (1.0 ng/kg)

| Subject # | Time (Minutes) | | | | | | | | | | | | | | | | | | | |
|---|---|---|---|---|---|---|---|---|---|---|---|---|---|---|---|---|---|---|---|---|
| | −20 | 0 | 20 | 40 | 60 | 80 | 100 | 120 | 140 | 160 | 180 | 200 | 220 | 240 | 260 | 280 | 300 | 320 | 340 | 360 |
| 01-001 | 16.8 | 17.4 | 10.4 | 7.6 | 1.9 | 2.4 | 1.1 | 0 | 0.8 | 2.4 | 2.6 | 13.2 | 15.9 | 12.9 | * | * | * | * | * | * |
| 01-002 | 17.1 | 18 | 15.6 | 8.4 | 4.2 | 3.5 | 2.2 | 1.6 | 2.6 | 3.1 | 4.5 | 6 | 5.6 | 6.3 | 7.5 | 7.7 | 10.5 | 10.1 | 14.2 | |
| 01-003 | 18.5 | 18 | 14 | 4 | 1.4 | 1.6 | 0.9 | 0.7 | 0.8 | 0 | 1.7 | 1.6 | 2.1 | 3.9 | 5.8 | 5.7 | 8.8 | 10.6 | 13.9 | 15.5 |
| 01-004 | 22 | 19.3 | 17.1 | 12.5 | 8.5 | 4.8 | 3.7 | 3.2 | 5 | 8.1 | 10 | 12.4 | 11.6 | 14.1 | * | * | * | * | * | * |
| 01-005 | 19.5 | 20 | 15.2 | 9.9 | 5.7 | 3 | 3 | 2.6 | 4.3 | 5.3 | 7.9 | 8.8 | 11.8 | 11.8 | 11.7 | * | * | * | * | * |
| 01-006 | 13 | 12.4 | 7.2 | 1.2 | 0.8 | 0.6 | 0.7 | 0.6 | 0.7 | 0.7 | 0.7 | 0.6 | 0 | 1.1 | 0.8 | 0.6 | 0.9 | 1.1 | 1 | 1.9 |
| 01-007 | 16 | 15.9 | 13.2 | 6.5 | 3.7 | 0 | 4.3 | 1.3 | 0 | 5.8 | 5.1 | 6.9 | 7.3 | 7.7 | 9 | 9.3 | 8.9 | 11.6 | 16 | 15.7 |
| 01-008 | 10.2 | 12.5 | 11.2 | 5.7 | 3.5 | 0 | 3.7 | 0 | 0 | 0 | 7.1 | 4.3 | 4.2 | 5.5 | 4.7 | 0 | 11.5 | 6.7 | 8 | 8.6 |
| Mean | 16.6 | 16.7 | 13.0 | 7.0 | 3.7 | 2.0 | 2.5 | 1.3 | 1.8 | 3.2 | 5.0 | 6.7 | 7.3 | 7.9 | 6.6 | 4.7 | 8.1 | 8.0 | 10.6 | 10.4 |

TABLE 6

Urine Output (2.0 ng/kg)

| Subject # | Time (Minutes) | | | | | | | | | | | | | | | | | | | |
|---|---|---|---|---|---|---|---|---|---|---|---|---|---|---|---|---|---|---|---|---|
| | −20 | 0 | 20 | 40 | 60 | 80 | 100 | 120 | 140 | 160 | 180 | 200 | 220 | 240 | 260 | 280 | 300 | 320 | 340 | 360 |
| 01-001 | 14.5 | 16 | 9.3 | 1.2 | 0 | 1.5 | 0 | 0 | 0.9 | 0 | 1 | 1.9 | 0.5 | 2.7 | 1.9 | 1.6 | 2.1 | 13.6 | 11.2 | 11.4 |
| 01-002 | 19.5 | 20 | 14.4 | 3 | 2.7 | 0 | 2.3 | 0 | 3.3 | 0.9 | 0.8 | 0.9 | 1.1 | 1.8 | 2.8 | 2.6 | 3.9 | 6.2 | 9.5 | 12.9 |
| 01-003 | 18.5 | 18.3 | 10.8 | 1.6 | 1.8 | 0 | 0 | 2.7 | 0 | 0 | 2.8 | 0 | 2.4 | 1.4 | 2 | 1.9 | 2 | 4.6 | 6.9 | 8.6 |
| 01-004 | 22 | 20.5 | 14.4 | 5.1 | 1.8 | 1.5 | 0.8 | 1 | 1.3 | 1.5 | 2 | 3.1 | 4.1 | 6 | 8.3 | 8.4 | 9.4 | 11.6 | 14.3 | 13.9 |
| 01-005 | 18 | 17.6 | 9.2 | 3.5 | 1.7 | 1.4 | 1.4 | 1 | 1.2 | 1.2 | 1.6 | 1.6 | 1.7 | 2.6 | 3.8 | 4.9 | 5.7 | 8.3 | 10.3 | 12.5 |
| 01-006 | 14 | 12.9 | 6.5 | 0.8 | 0.7 | 0.4 | 0.5 | 0.4 | 0.7 | 0.5 | 0.7 | 0.6 | 0.7 | 0.7 | 0.7 | 0.7 | 1 | 0.9 | 1 | 1.2 |

TABLE 6-continued

Urine Output (2.0 ng/kg)

| | Time (Minutes) | | | | | | | | | | | | | | | | | | | |
|---|---|---|---|---|---|---|---|---|---|---|---|---|---|---|---|---|---|---|---|---|
| Subject # | −20 | 0 | 20 | 40 | 60 | 80 | 100 | 120 | 140 | 160 | 180 | 200 | 220 | 240 | 260 | 280 | 300 | 320 | 340 | 360 |
| 01-007 | 14.5 | 13.2 | 9.1 | 0 | 0 | 0 | 0 | 0 | 0 | 4.6 | 0 | 0 | 0 | 1.7 | 0 | 0 | 0 | 7.3 | 6.5 | 9.1 |
| 01-008 | 14.5 | 13.1 | 10 | 2.9 | 1.6 | 0.5 | 0.9 | 0.4 | 0.4 | 0.5 | 0.4 | 0.4 | 0 | 1 | 0 | 0 | 1.4 | 0 | 3.5 | 4.6 |
| Mean | 16.9 | 16.5 | 10.5 | 2.3 | 1.3 | 0.7 | 0.7 | 0.7 | 1.0 | 1.2 | 1.2 | 1.1 | 1.3 | 2.2 | 2.4 | 2.5 | 3.2 | 6.6 | 7.9 | 9.3 |

As shown in Tables 1-6 and FIGS. 1-9, low doses of desmopressin administered as I.V. infusions over 2 hours produced significant antidiuretic effects in over-hydrated, normal subjects in a dose response fashion. These doses and calculated plasma/serum concentrations of desmopressin were far lower than the current labeled recommendations and current clinical practice by a factor of more than one order of magnitude. The pharmacodynamic duration of action was also proportional to the dose with the 1.0 and 2.0 ng/kg doses providing durations of 4 to 6 hours. This may be adequate to produce the desired therapeutic effects for existing and potential new clinical indications for desmopressin. Safety and tolerability were excellent.

The results of this study confirm the low-dose hypothesis for desmopressin and provide an empirical basis for further clinical studies in patients to evaluate low doses of desmopressin for such conditions as primary nocturnal enuresis, adult nocturia, incontinence and central diabetes insipidus.

The therapeutic effectiveness of desmopressin for all these clinical indications is based on desmopressin's antidiuretic pharmacological effect which results in production of smaller volumes of more concentrated urine. For patients with central diabetes insipidus, the pituitary gland produces little or no vasopressin, the natural antidiuretic hormone. This deficiency results in large volumes of very dilute urine being produced which can lead to dehydration and serious metabolic abnormalities unless the patient consumes very large volumes of water. Desmopressin replaces the deficient vasopressin and restores normal urine concentration and volume in these patients. In patients with primary nocturnal enuresis (bed wetting), the antidiuretic effect of desmopressin decreases urine volume at night, lowering the amount of urine which the urinary bladder must retain and, thereby decreasing or eliminating occurrences of enuresis.

In patients with adult nocturia, there is either polycoma (production of large amounts of urine) at night, low bladder capacity or increased bladder sensitivity to urine volume. Under all these circumstances, the bladder's threshold for urine retention is exceeded during the night, often several times, resulting in neurological signals for voiding. This awakens the patient in order to void. Desmopressin's antidiuretic effect decreases urine production at night delaying the time when the voiding threshold is exceeded resulting in a longer sleep period before voiding and decreasing the number of nocturnal voids.

In patients with incontinence of various types (stress, urge, etc.) often related to urinary bladder abnormalities from surgery, childbirth, and aging, the bladder is unable to retain even normal volumes of urine. The volume threshold for voiding is low and there is a high risk of involuntary voiding (incontinence). Desmopressin's antidiuretic effect decreases urine production allowing for voiding postponement because there is a delay in crossing the abnormally low volume threshold for voiding in these patients.

In all the above clinical indications, or medical uses of desmopressin, its antidiuretic pharmacological effect resulting in decreased production of more concentrated urine is the mechanism of therapeutic effectiveness. This clinical study demonstrates that desmopressin can produce this essential antidiuretic effect at much lower doses and lower blood concentrations than previously thought. Therefore, lower doses and concentrations of desmopressin may be used for treating patients with all of the above conditions.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A method for inducing voiding postponement in a patient while reducing the risk that the patient develops hyponatremia comprising delivering to the bloodstream of the patient an amount of desmopressin no more than about 2 ng/kg by intranasal, transdermal, intradermal, transmucosal, or conjunctival administration, said amount being therapeutically effective to produce an antidiuretic effect lasting for no more than between about 4 and about 6 hours.

2. The method of claim 1 comprising delivering to the bloodstream of the patient an amount of desmopressin no more than about 1 ng/kg.

3. The method of claim 1 further comprising advising a patient that fluid intake should be restricted after administration.

4. The method of claim 1 further comprising advising the patient that no water should be taken after administration.

5. The method of claim 1 comprising administering desmopressin to a patient suffering from nocturia, primary nocturnal enuresis (PNE), or incontinence.

6. The method of claim 1 wherein the method produces a plasma/serum desmopressin concentration in the patient of a maximum of no more than about 10 pg/ml.

7. The method of claim 1 wherein the method produces a plasma/serum desmopressin concentration in the patient of a maximum of no more than about 5 pg/ml.

8. A method for inducing voiding postponement comprising administering to a patient an amount of desmopressin sufficient to produce in the patient a urine osmolality ranging above about 300 mOsm/kg for less than about 5 hours after administration.

9. The method of claim 1 or 8 comprising administering the desmopressin by intranasal administration.

10. The method of claim 1 or 8 comprising administering the desmopressin by transdermal administration.

11. The method of claim 1 or 8 comprising administering the desmopressin by intradermal administration.

12. The method of claim 1 or 8 comprising administering the desmopressin by transmucosal administration.

13. The method of claim 1 or 8 comprising administering the desmopressin by conjunctival administration.

14. The method of claim 1 or 8 comprising administering to the patient between 100 and 2000 ng (0.1 µg to 2 µg) desmopressin.

15. The method of claim 8 wherein the method produces a plasma/serum desmopressin concentration in the patient no more than about 10 pg/ml.

16. The method of claim 8 wherein the method produces a plasma/serum desmopressin concentration in the patient no more than about 5 pg/ml.

17. The method of claim 8 comprising delivering to the bloodstream of the patient no more than about 2 ng/kg desmopressin.

18. The method of claim 8 comprising delivering desmopressin to the bloodstream of a patient suffering from nocturia, PNE, or incontinence.

19. A method for inducing voiding postponement in a patient while reducing the risk that the patient develops hyponatremia comprising delivering to the bloodstream of the patient via transdermal, intradermal, transmucosal, or conjunctival administration no more than about 1 ng/kg desmopressin to produce an antidiuretic effect for no more than about four to about six hours.

20. A method for inducing voiding postponement in a patient while reducing the risk that the patient develops hyponatremia comprising delivering to the bloodstream of the patient via intranasal administration no more than about 2 ng/kg of desmopressin so as to produce an antidiuretic effect.

21. The method of claim 20 comprising delivering to the bloodstream of the patient no more than about 1 ng/kg desmopressin.

* * * * *